US008389581B2

(12) United States Patent
DeMarco et al.

(10) Patent No.: US 8,389,581 B2
(45) Date of Patent: Mar. 5, 2013

(54) COMPOSITIONS AND METHODS FOR TREATING HOOF DISEASES

(75) Inventors: John P. DeMarco, Saratoga Springs, NY (US); Robert J. DeMarco, Saratoga Springs, NY (US)

(73) Assignee: Agrochem, Inc., Saratoga Springs, NY (US)

( * ) Notice: Subject to any disclaimer, the term of this patent is extended or adjusted under 35 U.S.C. 154(b) by 268 days.

(21) Appl. No.: 12/626,302

(22) Filed: Nov. 25, 2009

(65) Prior Publication Data

US 2010/0137451 A1 Jun. 3, 2010

Related U.S. Application Data

(60) Provisional application No. 61/200,367, filed on Nov. 28, 2008.

(51) Int. Cl.
*A61K 31/11* (2006.01)
(52) U.S. Cl. ....................... 514/693; 514/698
(58) Field of Classification Search ............... 514/693, 514/698
See application file for complete search history.

(56) References Cited

U.S. PATENT DOCUMENTS

| | | | |
|---|---|---|---|
| 4,859,694 A | 8/1989 | Pavlich | |
| 5,630,379 A | 5/1997 | Gerk et al. | |
| 5,692,570 A | 12/1997 | Akesson | |
| 5,772,985 A | 6/1998 | Kemp et al. | |
| 5,780,064 A | 7/1998 | Meisters et al. | |
| 6,364,025 B1 | 4/2002 | Jacobs | |
| 6,382,136 B1 * | 5/2002 | Bragulla et al. | 119/650 |
| 6,444,707 B1 | 9/2002 | Lampe et al. | |
| 6,596,325 B1 | 7/2003 | Vroom et al. | |
| 6,863,898 B2 | 3/2005 | Clawson | |
| 7,097,861 B1 | 8/2006 | O'Brien | |
| 7,332,151 B2 | 2/2008 | Yoder | |
| 7,533,733 B2 | 5/2009 | Nolan | |
| 7,661,393 B2 | 2/2010 | Torgerson et al. | |
| 7,670,629 B2 | 3/2010 | Baltzell | |
| 2004/0198639 A1 | 10/2004 | Patt | |
| 2007/0074672 A1 | 4/2007 | Torgerson et al. | |
| 2009/0110751 A1 | 4/2009 | Kenneke | |
| 2009/0178626 A1 | 7/2009 | Greeson | |

FOREIGN PATENT DOCUMENTS

| | | |
|---|---|---|
| CA | 1218302 | 2/1987 |
| DE | 4439572 | 5/1996 |
| GB | 2110084 | 6/1983 |
| WO | 2009053934 | 4/2009 |

OTHER PUBLICATIONS

International Search Report and Written Opinion of the International Searching Authority for PCT/US2009/065930 dated Feb. 22, 2010.
Kempson et al., "Use of Topical Disinfectant as part of a hoof care programme for horses with diseases of the hoof capsule." *Veterinary Record*, British Veterinary Association, London, GB, vol. 154, No. 21, May 22, 2004: 647-652.
Manske et al. "Topical treatment of digital dermatitis associated with severe heel-horn erosion in a Swedish dairy herd." *Preventative Veterinary Medicine*, vol. 53, No. 3, (2002): 215-231.
Thomsen et al., "Evaluation of Three Commercial Hoof Care Products Used in Footbaths in Danish Dairy Herds." *Journal of Dairy Science*, vol. 91, No. 4, (2008): 1361-1365.
Bedino, James, "Embalming Chemistry: Glutaraldehyde versus Formaldehyde." *Expanding Encyclopedia of Mortuary Practices*, No. 649. Springfield, The Champion Company, (2003), 2614-2632.
Glyoxal Cas N° .: 107-22-2, SIDS Initial Assessment Profile, UNEP Publications, 123-178, 2006.

* cited by examiner

*Primary Examiner* — Renee Claytor
(74) *Attorney, Agent, or Firm* — Heslin Rothenberg Farley & Mesiti P.C.

(57) ABSTRACT

The present invention is generally directed to compositions and methods for the treatment of an infectious disease of the foot of an animal. One aspect of the invention is directed to a method for preventing and/or treating one or more infectious diseases of the hoof in animals, comprising: preparing a copper-free and zinc-free composition comprising at least one cross-linking agent, wherein the cross-linking agent is not formaldehyde; and administering the composition to a lower leg and hoof area of said animal to prevent and/or treat said one or more infectious diseases. Another aspect of the invention is directed to a copper-free and zinc-free composition for the treatment and/or prevention of one or more infectious diseases of the hoof in animals, comprising at least one cross-linking agent, wherein said cross-linking agent is not formaldehyde. The present invention is also directed to a method for treating and/or preventing papillomatous digital dermatitis in an ungulate, comprising: preparing a copper-free and zinc-free composition comprising at least one cross-linking agent and at least one quaternary ammonium compound; and spraying or applying in a foam a therapeutically effective amount of said composition to a lower leg and hoof area of said ungulate in order to treat and/or prevent said papillomatous digitial dermatitis.

20 Claims, 7 Drawing Sheets
(7 of 7 Drawing Sheet(s) Filed in Color)

Cow 667 Before

Cow 667 After

Cow 89 Before

Cow 89 After

Cow 251 Before

Cow 251 After

COMPOSITIONS AND METHODS FOR TREATING HOOF DISEASES

1. CROSS-REFERENCE TO RELATED APPLICATIONS

This application claims priority to U.S. Provisional Application No. 61/200,367, filed Nov. 28, 2008, which is incorporated herein in its entirety by reference thereto.

2. TECHNICAL FIELD

The present invention relates to the treatment of a diseased animal. In particular, the present invention relates to compositions and methods useful for the treatment of one or more infectious diseases of a foot of an animal.

3. BACKGROUND OF THE INVENTION

Diseases among dairy herds dramatically impact the economics of animal production and milk production in the United States. It is estimated that the dairy cattle industry constitutes a significant contribution to the gross national product of the United States, accounting for an estimated $38 billion annually. A wide range of diseases, infections and injuries to the feet of animals, including cattle that are part of dairy herds, exist. Livestock in a dairy herd, for example, are susceptible to forming a variety of warts, abscesses, sole ulcers, foot rot, heel cracks and variations of lesions and infections on their feet and/or hooves, which may individually or collectively cause livestock to suffer lameness, clubbed hooves, loss of body weight, decreased milk production, and decreased rates of conception.

Infectious hoof diseases are common in farm animals such as sheep, goats, horses, dairy cows, and beef cattle. For example, hairy hoof warts, also referred to as digital dermatitis, hairy footwarts, strawberry or raspberry heelwarts or hairy heel warts, is a common disease condition in dairy cows and can cause lameness which leads to a decline in animal health and performance as measured by a decrease in body weight, fertility, and milk production. Since the late 1980's, bacterial diseases such as hairy heel warts have been a significant source of bovine lameness, and have had a significant economic impact on farmers.

Farmers have addressed this problem using a livestock footbath. The footbath holds a solution containing a substance to prevent and/or treat the disease, such as copper sulfate and/or zinc sulfate, or an antibiotic. Animals are forced to walk through the footbath to immerse the hooves in the treatment solution. For example, dairy cattle are usually led through a footbath on their way to or from the milking parlor. However, there are problems associated with the use of livestock footbaths, and they are not the most effective method of treatment and prevention of foot diseases. In particular, foot baths are inefficient and costly for at least one of the following reasons.

First, the length of the foot bath is directly correlated to the effectiveness of the treatment solution, with the longer the bath, the greater the duration of exposure to the treatment and prevention solution. The commonly used four foot long baths are not long enough for proper cleaning of the feet and subsequent exposure of the lesions to the treatment solution, especially since on average, animals walk through a traditional foot bath for five seconds or less. Moreover, manure attached to the animals hooves will commonly be carried into the foot bath or the animal may defecate into the foot bath, and since foot baths are liquid filled reservoirs that hold all environmental contaminants, the manure, mud and dirt rapidly degrade the treatment solution and render it ineffective. Also, most foot baths are permanently fixed and this prevents a farmer from locating the bath and treating the animals at different locations on the facility.

A further limitation to use of foot baths on farms is that they require a high level of management. The treatment solution requires changing at specified intervals after several animals pass through the bath in order to maintain efficacy of the treatment solution. If the foot bath is not changed and recharged accordingly, the efficacy of the treatment solution is greatly reduced. On a practical level, animals experiencing foot problems generally walk slower and are the last animals through the foot bath, when the bath is at its most inefficient, thereby decreasing the effectiveness of the treatment. Yet another limitation associated with the use of foot baths is that many of the products available for the treatment and prevention of foot diseases are not labeled for use in foot bath applications and are difficult to get into solution, for example, copper sulfate and zinc sulfate. Other products, including antibiotics, are not easy to use in the context of a foot bath, especially due to their cost and the fact that antibiotics degrade quickly when exposed to organic material.

Moreover, such footbaths as described supra may also cause pollution and injury to animals and humans. For example, discharge of copper sulfate, a compound commonly used in treating cows, from bath treatment systems into adjacent lands may cause significant damage. This is because most dairies dump the spent foot baths into a manure pit or a lagoon and the copper ultimately gets spread on production ground with the manure. The practice can lead to copper accumulation in the soil and after several years can accumulate in soil to levels that become toxic to soil microbes and crops. This can slow organic matter decomposition and nutrient cycling in soil and crop production could be reduced because of direct toxic effects of copper on the plants as well as reduced soil fertility. Importantly, copper accumulation in soil and forage can become toxic to sheep, whose tolerance for copper is much lower than that of dairy cattle. Toxic levels of copper in soil is a critical issue because there is no practical way to reverse the problem. Moreover, many large dairy farms use anaerobic digesters to produce methane gas from manure, and when copper sulfate can inhibit the bacteria's ability to produce methane gas in a digester lagoon.

Another chemical used in foot baths by the dairy industry is formaldehyde. Numerous burns to humans and animals result annually from use of formaldehyde; loss of eyesight and even death among workers have occurred. For these reasons the European Union has called for a ban of its use, and in the United States it has been listed as a known carcinogen.

In view of the problems outlined supra, there is a need for improved compositions and methods for treating one or more infectious diseases of a foot of an animal, including hairy heel warts.

4. SUMMARY OF THE INVENTION

The present invention is generally directed to compositions and methods for the treatment of an infectious disease of the foot of an animal. It has been surprisingly discovered that a spray or foam application of the presently taught novel and useful compositions offer more efficient and a better approach to treating one or more infectious diseases of a foot of an animal, including hairy heel warts.

One aspect of the invention is directed to a method for preventing and/or treating one or more infectious diseases of the hoof in animals, comprising: preparing a copper-free and zinc-free composition comprising at least one cross-linking agent, wherein the cross-linking agent is not formaldehyde; and administering the composition to a lower leg and hoof area of said animal to prevent and/or treat said one or more infectious diseases. In one embodiment, the animal has, or is at risk for, an infectious disease of the foot. In another embodiment, the infectious disease of the foot is hairy heel warts, foot rot, stable foot rot, or foot scald. In a related embodiment, the infection disease is papillomatous digital dermatitis. In one embodiment, the animal is an ungulate. In a related embodiment, the animal is a cow, sheep, horse, or goat.

In one embodiment, the administering step comprises spraying, splashing, or applying. In another embodiment, the administering step is in the form of a spray or foam, or a mixture thereof. In another embodiment, about three to about ten milliliters of the composition is sprayed on to the lower leg and hoof area of the animal. In another embodiment, the administering step is in the form of a gel.

In one embodiment, the infectious disease comprises an open lesion and after the administering step, said composition facilitates the rapid formation of a scab over said lesion. In another embodiment, the infectious disease comprises an open lesion on the lower leg and/or hoof area of said animal, and wherein after the administering step, said composition facilitates the rapid formation of a scab over said lesion within about twenty minutes. In one embodiment, the infectious disease comprises an open lesion on the lower leg and/or hoof area of said animal, and wherein about five to about fifteen minutes after the administering step, said composition causes the formation of a scab over said lesion. In another embodiment, after the administering step, the exposure time of said composition to a lower leg and hoof area of said animal is between about 5 to about 30 minutes. In another embodiment, the administering step includes periodic administrations. In one embodiment, the composition comprises at least one of colorants, skin conditioners, and buffers.

In one embodiment, the cross-linking agent is selected from the group consisting of glutaraldehyde, glyoxal, orthophthaldehyde, carbodiimides, diisocyanates, a formaldehyde donor, sodium hydroxymethyl glycinate, diazolidinyl urea, imidazolidinyl urea, dimethylol-5,5-dimethylhydantoin, dimethylol urea, 2-bromo-2-nitropropane 1,3-diol, quaternium-15, parabens, 5-chloro-2methylisothiazolin-3-one, 1,2-dibromo-2,4-dicyanobutane, ethanol and other alcohols, and polyol.

In another embodiment, the cross-linking agent is selected from the group consisting of aldehydes, such as glyceraldehyde, glutaraldehyde, dextran dialdehyde, and carbohydrates; diols, such as ethylene glycol, di(ethylene glycol), polyethylene glycol, propylene glycol, di(propylene) glycol, polypropylene glycol; unsaturated diesters such as ethylene glycol dimethacrylate, di(ethylene glycol) dimethacrylate, poly(ethylene glycol) dimethacrylate, poly(lauryl methacrylate-co-ethylene glycol dimethacrylate), propylene glycol dimethacrylate, di(propylene glycol) dimethacrylate, poly(propylene glycol) dimethacrylate; dihydrazides such as malonic dihydrazide, ethylmalonic dihydrazide, succinic dihydrazide, glutaric dihydrazide, adipic dihydrazide, isophthalic dihydrazide, oxalyl dihydrazide, pimelic dihydrazide, 3,3'-sulfonyldibenzenesulfonic dihydrazide; diisocyanates such as m-xylylene isocyanate, 4-methyl-m-phenylene diisocyanate, 2-methyl-m-phenylene diisocyanate, 3,3'-dimethoxy-4,4'-biphenylene diisocyanate, 4-Br-6-methyl-1,3-phenylene diisocyanate, 4-Cl-6-methyl-1,3-phenylene diisocyanate, toluene 2,4-diisocyanate, 1,3-phenylene diisocyanate, 1,4-phenylene diisocyanate, 2,4,6-trimethyl-1,3-phenylene diisocyanate, 1,4-diisocyanatebutane, 1,6-diisocyanatehexane, 1,8-diisocyanateoctane, isophorone diisocyanate; carbodiimides such as N,N-(3-dimethylaminopropyl)-N-ethyl carbodiimide (EDC); salts, such as $CaCl_2$; divinylsulfone, sulfonylurea, hydrolysable polyrotaxane, L-lysine methyl ester, and genipin. In one embodiment, the one or more cross-linking agents of the present invention are present in the composition at a level from 5% to 30%.

In one embodiment, the composition further comprises at least one antimicrobial essential oil or at least one active thereof or a mixture thereof. In a related embodiment, the antimicrobial essential oil is selected from the group consisting of those obtained from thyme, lemongrass, citrus, lemons, orange, anise, clove, aniseed, pine, cinnamon, geranium, roses, mint, lavender, citronella, eucalyptus, peppermint, camphor, ajowan, sandalwood, rosmarin, vervain, fleagrass, lemongrass, ratanhiae, cedar and mixtures thereof. In another related embodiment, the actives of essential oil is selected from the group consisting of thymol, eugenol, menthol, geraniol, verbenone, eucalyptol, pinocarvone, cedrol, anethol, carvacrol, hinokitiol, berberine, ferulic acid, cinnamic acid, methyl salicylic acid, methyl salycilate, terpineol, limonene and mixtures thereof. In another embodiment, the antimicrobial essential oil or active thereof or mixture thereof is present in the composition at a level from 0.03% to 3%.

In one embodiment, the composition further comprises at least one poly(alkylene glycol) alkyl ether. In a related embodiment, the poly(alkylene glycol) alkyl ether is selected from the group consisting of poly(propylene glycol) mono butyl ether, poly(ethylene glycol-co-propylene glycol) mono butyl ether, poly(ethylene glycol) dimethyl ether, poly(ethylene glycol-co-propylene glycol) dimethyl ether, poly(ethylene glycol) stearate or mixtures thereof. In another embodiment, the apoly(alkylene glycol) alkyl ether is present in the composition at a level from 0.03% to 3%.

In one embodiment, the composition further comprises at least one gelling agent. In one embodiment, the gelling agent is selected from the group consisting of naturally-occurring polymeric materials such as locust bean gum, guar gum, sodium alginate, sodium caseinate, egg albumin, gelatin agar, carrageenin gum, sodium alginate, xanthan gum, quince seed extract, tragacanth gum, starch, chemically modified starches, semi-synthetic polymeric materials such as cellulose ethers (e.g. hydroxyethyl cellulose, methyl cellulose, carboxymethyl cellulose, hydroxy propylmethyl cellulose), hydroxypropyl guar gum, soluble starch, cationic celluloses, cationic guars, carboxyvinyl polymers, polyvinylpyrrolidone, polyvinyl alcohol, polyacrylic acid polymers, polymethacrylic acid polymers, polyvinyl acetate polymers, polyvinyl chloride polymers, acrylic acid/ethyl acrylate copolymers, carboxyvinyl polymers, and polyvinylidene chloride polymers. In another embodiment, the at least one gelling agent comprises naturally-occurring polymeric materials, chemically modified starches, semi-synthetic polymeric materials, synthetic polymeric materials, acrylic acid/ethyl acrylate copolymers and carboxyvinyl polymers.

In one embodiment, the at least one gelling agent is locust bean gum, guar gum, sodium alginate, sodium caseinate, egg albumin, gelatin agar, carrageenin gum, sodium alginate, xanthan gum, quince seed extract, tragacanth gum, starch, a cellulose ether, hydroxypropyl guar gum, soluble starch, cationic cellulose, cationic guar, a carboxyvinyl polymer, polyvinylpyrrolidone, polyvinyl alcohol, a polyacrylic acid polymer, a polymethacrylic acid polymer, a polyvinyl acetate polymer a, a polyvinyl chloride polymer, a polyvinylidene chloride polymer, a polyalkenyl polyether cross-linked polymer of acrylic acid, or a mixture thereof. In another embodiment, the at least one gelling agent is hydroxypropylmethyl cellulose, hydroxyethyl cellulose, methyl cellulose, carboxymethyl cellulose, or a mixture thereof. In a related embodiment, the gelling agent is xanthan gum. In another embodiment, the gelling agent is present in the composition at a level from 0.03% to 3%.

In one embodiment, the composition further comprises at least one quaternary ammonium compound. In one embodiment, the quaternary ammonium compound is selected from the group consisting of quaternary ammonium compounds containing alkyl or substituted alkyl groups, alkyl amide and carboxylic acid groups, ether groups, unsaturated alkyl groups, and cyclic quaternary ammonium compounds. These compounds can be chlorides, dichlorides, bromides, methylsulphates, chlorophenates, cylcohexylsulphamates or salts of the other acids. In another embodiment, the quaternary ammonium compound is selected from the group consisting of alkylpyridinium chlorides and/or sulphates, the alkyl group being preferably cetyl, dodecyl or hexadecyl group, alkylisoquinolyl chlorides and/or bromides, the alkyl group being preferably dodecyl group, octyl decyl dimethyl ammonium chloride, dioctyl dimethyl ammonium chloride, didecyl dimethyl ammonium chloride, alkyl dimethyl benzyl ammonium chloride, alkyl dimethyl benzyl ammonium chloride wherein the alkyl is one or more of $C_{12}$ $C_{14}$ and $C_{16}$ alkyl, alkyl dimethyl ammonium saccharinate, cetylpyridinium and mixtures thereof. In one embodiment, the quaternary ammonium compound is selected from the group consisting of n-alkyl dimethly benzyl ammonium chloride, dialkyl dimethly ammonium chloride, or a mixture thereof. In another embodiment, the at least one quaternary ammonium compound is present in the composition at a level from 5% to 20%.

In one embodiment, the composition further comprises at least one surfactant. In another embodiment, the composition further comprises at least one surfactant selected from the group consisting of nonionic, semi-polar, anionic, cationic, zwitterionic, and amphoteric surfactants. In another embodiment, the composition further comprises a surfactant selected from the group consisting of polyoxyethylene alcohols, alkyl ether sulfates, and alkyl sulfates. In another embodiment, the composition further comprises about 0.03% to 5% by weight of a surfactant.

In another embodiment, the composition further comprises at least one surfactant selected from the group consisting of glycoside, glycols, ethylene oxide and mixed ethylene oxide/propylene oxide adducts of alkylphenols, the ethylene oxide and mixed ethylene oxide/propylene oxide adducts of long chain alcohols or of fatty acids, mixed ethylene oxide/propylene oxide block copolymers, esters of fatty acids and hydrophilic alcohols, sorbitan monooleates, alkanolamides, soaps, alkylbenzene sulfonates, olefin sulfonates, paraffin sulfonates, propionic acid derivatives, alcohol and alcohol ether sulfates, phosphate esters, amines, amine oxides, alkyl sulfates, alkyl ether sulfates, sarcosinates, sulfoacetates, sulfosuccinates, cocoamphocarboxy glycinate, salts of higher acyl esters of isethionic acid, salts of higher acyl derivatives of taurine or methyltaurine, phenol poly ether sulfates, higher acyl derivatives of glycine and methylglycine, alkyl aryl polyether alcohols, salts of higher alkyl substituted imadazolinium dicarboxylic acids, ferchorics, tannics, naphthosulfonates, lauryl sulfate, laurylether sulfate, cocamidopropylbetaine, alkyl polyglycosides, amine oxides, monochloracetics anthraflavinics, hippurics, anthranilics, naphthoics, phthalics, carboxylic acid salts, acrylic acids, phosphates, alkylamine ethoxylates, ethylenediamine alkoxylates, betaines, sulfobetaines, imidazolines, polyoxyethylene alcohols, alkyl ether sulfates, and alkyl sulfates. In one embodiment, the composition further comprises one or more ethoxylated nonlyphenols.

One aspect of the present invention is directed to a copper-free and zinc-free composition for the treatment and/or prevention of one or more infectious diseases of the hoof in animals, comprising at least one cross-linking agent, wherein said cross-linking agent is not formaldehyde. In one embodiment, the composition comprises about 5% to about 30% by weight of at least one cross-linking agent; about 5% to 20% by weight of at least one quaternary ammonium compound; about 0.03% to 3% by weight of at least one apoly(alkylene glycol) alkyl ether; about 0.03% to 3% by weight of at least one gelling agent; about 0.03% to 3% by weight of at least one antimicrobial essential oil or active thereof; and about 0.03% to 5% by weight of at least one surfactant.

One aspect of the present invention is directed to a composition for the treatment and/or prevention of one or more infectious diseases of the hoof in animals, comprising one or more cross-linking agents, excluding formaldehyde; one or more quaternary ammonium compounds; one or more gelling agents; one or more surfactants; one or more antimicrobial essential oils or actives thereof; and one or more poly(alkylene glycol) alkyl ethers.

One aspect of the present invention is directed to a method for treating and/or preventing papilomatous digital dermatitis in an ungulate, comprising: preparing a copper-free and zinc-free composition comprising at least one cross-linking agent and at least one quaternary ammonium compound; and spraying or applying in a foam a therapeutically effective amount of said composition to a lower leg and hoof area of said ungulate in order to treat and/or prevent said papillomatous digitial dermatitis.

5. BRIEF DESCRIPTION OF THE FIGURES

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

6. DETAILED DESCRIPTION OF THE INVENTION

Figure 1:
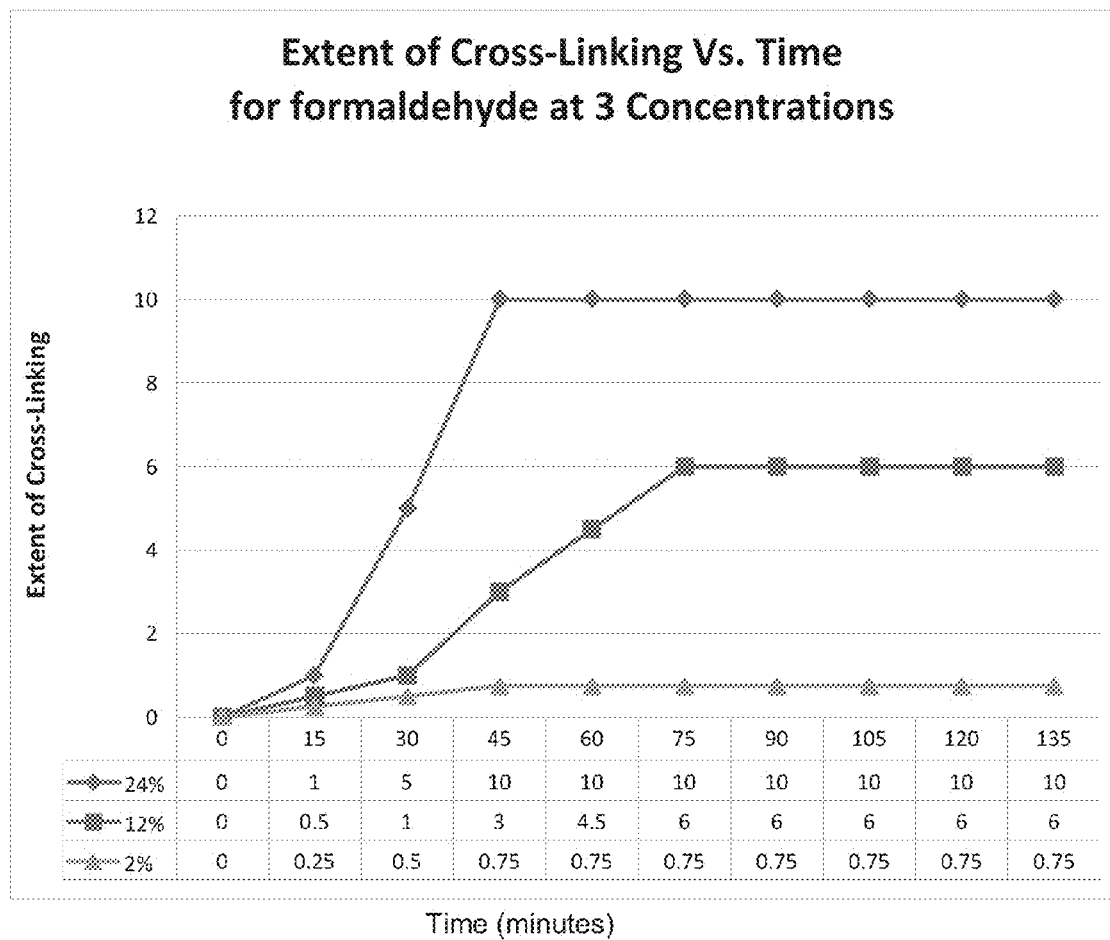
FIG. 1 is a line graph showing the extent of cross-linking of the protein medium over time where three dilutions of formaldehyde 37% was used.

In accordance with the present invention, it has been discovered that compositions of the present invention can be used to control diseases of the hoof, such as foot warts, hoof rot, and other bacterial hoof conditions more effectively than other products.

It has been discovered that a novel composition and a method of administering it is highly effective at treating and/or preventing infectious diseases of the foot of an animal, including hairy heel warts. Unlike compositions comprising formaldehyde, the presently taught composition has no obnoxious odors and unlike solutions containing copper, the present composition is biodegradable. Some of the treatments available use antimicrobials in footbaths in order to kill the bacteria associated with the disease condition, however, once the animal leaves the footbath, the open wart is prone to being re-infected as the cow walks into bacteria infested mud and manure.

The presently taught composition possesses germicidal components and are formulated so that after their administration, the composition facilitates creation of a natural scab where the infectious disease may have caused ulcers. Formation of a scab is important because it stops the outward progression of the destructive bacteria, providing a tough waterproof barrier which prevents contamination and re-infection, and allows the animals' immune system to begin the healing process. Formation of the scab occurs rapidly through a process known as cross-linking which occurs to the protein fibers in the open wound. One of the advantageous properties of the presently taught composition over existing treatments, is the rapid nature in which the composition promotes formation of a scab. In addition, unlike other treatments, the presently taught composition does not affect normal skin.

Infectious diseases of the hoof, such as hairy heel warts (papillomatous digital dermatitis, or "PDD") hoof rot (interdigital phlegmon), and stable hoof rot (interdigital dermatitis) are common in farm animals such as sheep, goats, horses, dairy cows, and beef cattle. The benefits of the compositions and methods of the present invention for treating and/or preventing diseases of the foot of an animal over other compositions and methods include efficacious non-toxic compositions, maintenance of low levels of infectious diseases, and/or reduced amounts of copper being transferred to the soil and water. In particular, the present invention teaches formulating the unique composition in a unique way as a spray or foam, and such means of administering the composition of the present invention has superior benefits to existing methods for treating and/or preventing diseases of the foot of an animal, including hairy heel warts.

Hairy heel warts, also referred to as digital dermatitis, hairy footwarts, strawberry or raspberry heelwarts or hairy hoof warts, is a common disease condition in dairy cows. These diseases can cause lameness, leading to animals walking on toes and decreased body weight, fertility and milk production, with the seriously afflicted animals being culled. Clinically, hairy heel warts typically appear as a lameness outbreak of variable severity within dairy herds. It is a superficial skin disease of the bovine digit with variable presentation, depending on the stage of the lesion, from painful, moist, strawberry-like lesions to raised, hairy, wart-like lesions. These lesions are generally located on the rear of the foot between the bulbs of the heel. Since the late 1980's, such bacterial diseases have harmed livestock and have caused significant economic losses for affected dairy producers.

Hairy heel warts is a contagious disease, based on the spread of disease regionally, high levels of disease within affected herds, within-herd spread after introduction of affected cattle, and higher prevalence in younger cows and that large herd size, the amount of moisture in corrals where cows walk, and the introduction of dairy replacement heifers are contributing factors to disease occurrence. The exact causative agent for hairy heel warts is not known, however evidence suggests that one or more species of spirochete of the genus *Treponema* is responsible. *Treponema* bacteria can be anaerobic or microaerophilic (require oxygen at less than atmospheric levels) and can be parasitic to humans and to animals causing a range of diseases. Mud and manure slurry found in dairy free stall environments are an ideal environment for *Treponema* bacterial to thrive.

The lesions characteristic of hairy heel warts are generally, but not always, at the back of the foot near interdigital cleft and heel. Sometimes the lesions are at the front of the foot, in the interdigital cleft or near dewclaws. An early lesion is sharply demarcated, flat, dime-sized, round to oval, moist, tufted, strawberry-like surface. A mature lesion, however, is larger (up to two inches across), usually is raised, and sometimes with long brown/black tufts or hair-like, tissue projections on the surface. Long hairs can be present on edge of the lesion. The lesions can be very painful to the animal and persist for many months, having direct and indirect physiological effect on the animal.

Hoof rot, or interdigital phlegmon, is an infection of the soft tissue between the claws of the feet. In equine animals, it is also known as hoof thrush. Here, the term "hoof rot" will be used to indicate both hoof rot and hoof thrush. Hoof rot is caused by the anaerobic bacterium, *Fusobacterium necrophorum*. The anaerobes *Dichelobacter* (*Bacteriodes*) *nodosus* and *Prevotella melaminogenicus* have also been implicated. The bacteria invade the skin of the foot at injured or damaged skin areas, and initially cause a painful swelling of the skin between the claws. A fissure or crack then develops along the swollen area for part or all of the length of the interdigital space. If left untreated, hoof rot can enter the joints, bones, and/or tendons of the foot, making recovery from the infection unlikely. Animals with hoof rot can have a mild fever, loss of appetite and accompanying weight loss, and develop mild to severe lameness.

Interdigital dermatitis, or stable hoof rot, is generally a chronic inflammation of the skin in the area between the toes of the feet (interdigital cleft). This infection is caused by the bacterium *Dichelobacter nodosus*. The skin in the area of the interdigital cleft will appear puffy with a dry exudation which will cause a crust to form. The condition may occasionally cause lameness or heel crack/heel erosion but generally results in an alteration in the animal's gait.

Control of hairy warts and associated foot diseases has proven difficult. At present, one effective treatment of hoof warts, hoof rot and stable hoof rot is the use of antibiotics, such as tetracycline, lincomycin, spectinomycin, penicillin, oxytetracycline, and ampicillin, which are topically applied to the affected area via use of footbaths. Most commercial foot baths are thirty inches wide, four feet long and six inches deep, and require about thirty five gallons of treatment solution. Where footbaths are used, the animal is led to walk through while either entering or exiting particular areas, such as for example milking parlors, shearing stalls, or feeding stalls, the footbath to immerse the hooves in a treatment solution, containing an antibiotic or other material such as copper sulfate and/or zinc sulfate.

However, there are problems associated with the use of livestock footbaths as detailed supra. For example, bacteria-containing organic materials on the hooves of the animals are washed off in the footbath solution. The organic materials build up over time and overcome the ability of the material in the solution to prevent and/or treat the disease. In some cases, the footbath can even become a breeding ground for bacteria, and can thus actually accelerate the spread of an infectious hoof disease, rather than treat and/or prevent it. Additionally, disposal of the footbath water may raise environmental concerns, as several states are mandating the discontinued use of products containing heavy metals such as copper.

Application of oxytetracycline under a bandage can be effective, but bandaging affected hooves may be labor-intensive in large or heavily afflicted herds. Even though antibiotics can be effective in treating these infectious diseases, there are also several drawbacks to their use, including their expense and the concern, especially with dairy cows, that the use of antibiotics may result in the presence of antibiotic residues in the animal or its milk. Further, extended use of antibiotics may result in the development of an antibiotic-resistant bacteria strain. Finally, the use of antibiotics for the treatment of hoof rot, stable hoof rot or hairy heel warts is "off-label," that is, the antibiotics are not specifically approved for these uses.

In order to treat and prevent hoof rot, hairy heel warts, and stable hoof, chemical-based germicides have also been tried as a treatment. Although some germicides, such as those containing copper sulfate and zinc sulfate, have some efficacy against hoof rot and stable hoof rot, they are ineffective against hairy heel warts. Many of the available compounds are expensive and/or ineffective at high dilutions, such as those used in foot baths. Likewise, combinations of hydrogen peroxide and peracetic acid have been used, but also are not effective against hairy heel warts, and suffer from stability and storage problems, as well as the problem that the chemical combination irritates the hoof at the recommended treatment concentrations.

Hairy heel warts have been treated in a number of ways. One form of control is to treat the larger clinically active lesions, which are a source of infection, by surgical removal, although additional treatments for complete healing may be necessary. This process is laborious, time consuming and expensive, particularly when dealing with large herds. There have been anecdotal reports of success with formaldehyde against hairy heel warts, however, this agent is classified as a carcinogen and toxin, and is illegal in some parts of the United States. Further, use of too high a concentration of formaldehyde can result in destruction of healthy hoof tissue, or can even lead to sloughing of the hoof. Thus, the use of formaldehyde is not desired in treating hairy heel warts and other diseases of the hoof.

The present invention addresses the need for a composition that is effective against foot rot, stable foot rot, and hairy heel warts, that is affordable, copper-free and zinc-free, and that avoids the use of antibiotics. The present invention also addresses the need for an effective method of both treating and/or preventing foot rot, stable foot rot, and hairy heel warts. A novel composition has been discovered which is highly effective at treating infectious diseases of the foot of an animal, including hairy heel warts when applied to the lower leg and hoof area of the animal as a spray or foam. This approach provides a more efficient and selective means by which infectious diseases of the foot of an animal, including hairy heel warts can be treated and/or prevented in animals, including cows. One of the advantageous properties of the presently taught composition is the rapid nature in which the composition promotes formation of a scab over a lesion that may have formed.

One aspect of the present invention is directed to a method for preventing and/or treating one or more infectious diseases of the hoof in animals, comprising: preparing a copper-free and zinc-free composition comprising at least one cross-linking agent, wherein the cross-linking agent is not formaldehyde; and administering the composition to a lower leg and hoof area of said animal to prevent and/or treat said one or more infectious diseases. The animal has, or is at risk for, an infectious disease of the foot, and the infectious disease of the foot is hairy heel warts, foot rot, stable foot rot, or foot scald. The animal to be treated is commonly a cow, sheep, horse, or goat.

The method of the present invention includes administering the novel composition in the form of a spray or foam, or a mixture thereof. Generally, about three to about ten milliliters of the composition is sprayed on to the lower leg and hoof area of the animal, and in particular to the site of any lesion. The composition may also be administered in the form of a gel to the lower leg and hoof area of the animal. Where the infectious disease comprises an open lesion, administration of the composition facilitates the rapid formation of a scab over said lesion, which can occur within about five to about fifteen minutes. This rapid formation of a scab is a desirable quality of the present composition and is achieved in part by the novel means of administering the novel composition. The administering step may include periodic administrations of the composition, and the composition may comprise at least one of colorants, skin conditioners, and buffers.

In some embodiments, the animal has, or is at risk for, an infectious disease of the foot. As an example, an animal can be in need of treatment with the compositions described herein when the animal is diagnosed with hairy heel warts, foot rot, and/or scald. As another example, an animal can be in need of treatment with the compositions described herein when the animal is determined at risk for hairy heel warts, foot rot, and/or scald. Diagnosis of infectious diseases of the foot in animals is within the skill of the art. The determination of risk for an infectious disease of the foot can be according to environmental conditions, susceptibility of certain types of animals, or other factors known to one of skill in the art.

6.1 Definitions

As used in this document, the term foot as used in this document means not only the terminal part of a vertebrate animal's leg, but also the hoof (the curved covering of horn that protects the front of the terminal part), the pad, the pastern, the dewclaw, the hock, and the portion of the leg below the knee or hock on an animal such as a domestic bovine.

As used herein, treatment is generally understood to encompass both prophylactic treatment as well as treatment of an existing or diagnosed condition. For example, an animal in need of treatment can be at risk, or determined to be at risk, for an infection of the foot. As another example, an animal in need of treatment can have, or be diagnosed as having, an infection of the foot. Diagnosis and risk assessment for animal foot diseases discussed herein is within the skill of the art. In some cases (e.g., with hoof rot), the treatment is preferably to increase hoof hardness, thus helping to prevent the infection.

The term ungulate is understood to include an animal having hooves, or feet resembling hooves, or feet that are hoof-like. An ungulate is also understood to include an animal of, or belonging to, the former order Ungulata, now divided into the orders Perissodactyla and Artiodactyla and composed of hoofed mammals such as, but not limited to, a horse, a cow, a goat, a sheep, a pig, deer, an elephant, an elk, a bison, a moose, a gazelle, and an antelope. The term debris means at least animal waste.

The term ingredients means any combination of active and inert chemicals and fluids, including water, that may be discharged from dispensers for treating animal foot problems including, without limitations, diseases, infections, abrasions, and injuries to a foot of an animal, as well as preventative ingredients including, for example, those useful for creating resistance to diseases and lacerations, for hardening hooves, and similar desirable treatments.

6.2 Compositions and Methods

The subject invention provides an inexpensive, easy to use, highly effective, composition and method of treating and/or preventing infectious diseases of hoofed animals, including hairy hoof warts. One aspect of the present invention is directed to a method for preventing and/or treating one or more infectious diseases of the hoof in animals, comprising: preparing a copper-free and zinc-free composition comprising at least one cross-linking agent, wherein the cross-linking agent is not formaldehyde; and administering the composition to a lower leg and hoof area of said animal to prevent and/or treat said one or more infectious diseases. Formaldehyde is the simplest and smallest aldehyde which under certain conditions can make it effective, however dangerous. Di-aldehydes are a bit larger, less reactive, but exhibit good crosslinking because of their two aldehyde groups.

The cross-linking agents of the present invention are selected from the group consisting of aldehydes, such as glyceraldehyde, glutaraldehyde, dextran dialdehyde, and carbohydrates; diols, such as ethylene glycol, di(ethylene glycol), polyethylene glycol, propylene glycol, di(propylene) glycol, polypropylene glycol; unsaturated diesters such as ethylene glycol dimethacrylate, di(ethylene glycol) dimethacrylate, poly(ethylene glycol) dimethacrylate, poly (lauryl methacrylate-co-ethylene glycol dimethacrylate), propylene glycol dimethacrylate, di(propylene glycol) dimethacrylate, poly(propylene glycol) dimethacrylate; dihydrazides such as malonic dihydrazide, ethylmalonic dihydrazide, succinic dihydrazide, glutaric dihydrazide, adipic dihydrazide, isophthalic dihydrazide, oxalyl dihydrazide, pimelic dihydrazide, 3,3'-sulfonyldibenzenesulfonic dihydrazide; diisocyanates such as m-xylylene isocyanate, 4-methyl-m-phenylene diisocyanate, 2-methyl-m-phenylene diisocyanate, 3,3'-dimethoxy-4,4'-biphenylene diisocyanate, 4-Br-6-methyl-1,3-phenylene diisocyanate, 4-Cl-6-methyl-1,3-phenylene diisocyanate, toluene 2,4-diisocyanate, 1,3-phenylene diisocyanate, 1,4-phenylene diisocyanate, 2,4,6-trimethyl-1,3-phenylene diisocyanate, 1,4-diisocyanatebutane, 1,6-diisocyanatehexane, 1,8-diisocyanateoctane, isophorone diisocyanate; carbodiimides such as N,N-(3-dimethylaminopropyl)-N-ethyl carbodiimide (EDC); salts, such as $CaCl_2$, divinylsulfone, sulfonylurea, hydrolysable polyrotaxane, L-lysine methyl ester, and genipin. Cross-linking may also be carried out or aided by one or more enzymes.

In another embodiment, the cross-linking agent is selected from the group consisting of glutaraldehyde, glyoxal, ortho-phthaldehyde, carbodiimides, diisocyanates, a formaldehyde donor, sodium hydroxymethyl glycinate, diazolidinyl urea, imidazolidinyl urea, dimethylol-5,5-dimethylhydantoin, dimethylol urea, 2-bromo-2-nitropropane 1,3-diol, quaternium-15, parabens, 5-chloro-2methylisothiazolin-3-one, 1,2-dibromo-2,4-dicyanobutane, ethanol and other alcohols, and polyol. In one embodiment, the composition of the present invention comprises glutaraldehyde, glyoxal, ortho-phthaldehyde or mixtures thereof.

Glutaraldehyde is a four carbon molecule terminated at both ends by aldehyde groups. It is widely used by light and electron microscopists for its efficacy in preserving cellular structure. It was conceived that glutaraldehyde would be useful in the context of the present invention because glutaraldehyde would not overly dry the treated area or cause the treated area or hooves to become brittle. Further, it was conceived that glutaraldehyde's comparatively high molecular weight would aid to limit its ability to diffuse into the tissue, especially since as the tissue is cross-linked, its ability to penetrate over time diminishes. One of the added benefits of the presently taught composition is that it limits the function of the composition to the superficial skin layers preventing the composition from being too aggressive and penetrating too deeply into the treated area. Moreover, whereas formaldehyde is known to cause chemical burns even to healthy tissue, use of glutaraldehyde as the cross-linking agent of the presently taught composition allows unscathed skin to remain healthy.

Penetration and diffusion rates for glutaraldehyde are very slow with typical values of under about 5 mm of penetration on rat brain overnight. This is in sharp contrast to formaldehyde, which exhibits fast penetration/diffusion rates but slow endpoint fixation rates. It was conceived that since manure/urine and mud slurry found on dairy farms typically have a pH of around 8, a cross-linking agent such as glutaraldehyde would be effective, whereas such organic loading would essentially render formaldehyde and many other germicides ineffective.

Glutaraldehyde is a strong germicide and a cross-linking agent which rapidly fixes or binds loose protein fibers. Glutaraldehyde is an effective biocide and another of the advantageous properties of the present composition is that glutaraldehyde minimally penetrates into the tissue, thereby reducing the extent to which it may circulate in the blood stream and reach vital organs. Glyoxal is an organic compound used as a solubilizer and cross-linking agent in polymer chemistry. It is typically supplied as a 40% aqueous solution.

The one or more cross-linking agents of the present invention are present in the composition at a level from 0.001% to 30%. In one embodiment, the one or more cross-linking agents of the present invention are present in the composition at a level from 0.5% to 20%. In another embodiment, the one or more cross-linking agents of the present invention are present in the composition at a level from 1% to 15%. In yet another embodiment, the one or more cross-linking agents of the present invention are present in the composition at a level from 1% to 10%. In another embodiment, the one or more cross-linking agents of the present invention are present in the composition at a level from 5% to 13%. In yet another embodiment, the one or more cross-linking agents of the present invention are present in the composition at about 10%. In yet another embodiment, the one or more cross-linking agents of the present invention are present in the composition at about 25%. In one embodiment, the one or more cross-linking agents of the present invention are present in the composition at a level from 5% to 30%. In another embodiment, the one or more cross-linking agents of the present invention are present in the composition at a level of about 40% to about 50%.

In one embodiment, the composition of the present invention comprises an antimicrobial essential oil or an active thereof or mixture thereof, which contribute anti-microbial and bacterial properties to the composition. Suitable antimicrobial essential oils for use herein are those essential oils which exhibit antimicrobial activity. By "actives of essential oils", it is meant herein any ingredient of essential oils that exhibit antimicrobial activity. It is speculated that said antimicrobial essential oils and actives thereof act as proteins denaturing agents.

Such antimicrobial essential oils include, but are not limited to, those obtained from thyme, lemongrass, citrus, lemons, orange, anise, clove, aniseed, pine, cinnamon, geranium, roses, mint, lavender, citronella, eucalyptus, peppermint, camphor, ajowan, sandalwood, rosmarin, vervain, fleagrass, lemongrass, ratanhiae, cedar and mixtures thereof.

Actives of essential oils to be used herein include, but are not limited to, thymol (present for example in thyme, ajowan), eugenol (present for example in cinnamon and clove), menthol (present for example in mint), geraniol (present for example in geranium and rose, citronella), verbenone (present for example in vervain), eucalyptol and pinocarvone (present in eucalyptus), cedrol (present for example in cedar), anethol (present for example in anise), carvacrol, hinokitiol, berberine, ferulic acid, cinnamic acid, methyl salicylic acid, methyl salycilate, terpineol, limonene and mixtures thereof. In one embodiment, the composition of the present invention comprises methyl salycilate.

Thymol may be commercially available for example from Aldrich—Manheimer Inc, eugenol may be commercially available for example from Sigma, Systems—Bioindustries (SBI)—Manheimer Inc. In one embodiment, the composition further comprises a component selected from the group consisting of antimicrobial essential oils and actives thereof, quaternary ammonium compounds, paraben, aldehydes, phenolic compounds, alcohols, organic acids, chlorine-type bleaches, and mixtures thereof.

The antimicrobial essential oil or active thereof or mixture thereof is present in the composition at a level up to 20% by weight of the total composition. In one embodiment, the level is at least 0.003% to 10%. In another embodiment, the antimicrobial essential oil or active thereof or mixture thereof is present in the composition at a level from 0.006% to 10%. In another embodiment, the antimicrobial essential oil or active thereof or mixture thereof is present in the composition at a level from 0.01% to 8%. In another embodiment, the antimicrobial essential oil or active thereof or mixture thereof is present in the composition at a level from 0.03% to 3%.

In one embodiment, the composition of the present invention comprises propylene glycol or an equivalent thereof. In one embodiment, the composition of the present invention comprises a poly(alkylene glycol) alkyl ether, as defined herein after, or a mixture thereof. Suitable poly(alkylene glycol) alkyl ethers for use herein include poly(propylene glycol) mono butyl ether, poly(ethylene glycol-co-propylene glycol) mono butyl ether, poly(ethylene glycol) dimethyl ether, poly(ethylene glycol-co-propylene glycol) dimethyl ether, poly(ethylene glycol) stearate or mixtures thereof. Poly(propylene glycol) mono butyl ether (average molecular weight 340) is commercially available from Aldrich or from Union Carbide under Ucon-lb 65™.

Propylene glycol can serve as an anti-freeze. One advantageous property of the presently taught composition is that it is useful in cold climates when traditional techniques for treating hairy heel warts fail due to cold weather. Colder temperatures are known to reduce the effectiveness of formaldehyde and other agents, whereas glutaraldehyde retains its effectiveness in colder weather. Colder temperatures can also cause freezing of footbaths containing conventional solutions. Propylene glycol can also serve as an emollient/skin conditioner used to combat potential dryness that can result from the fixing agent. Propylene glycol also serves as a carrier and gelling agent like xantham gum, albeit to a lesser extent.

The poly(alkylene glycol) alkyl ether or a mixture thereof is present in the composition at a level from 0.001% to 10%. In one embodiment, the poly(alkylene glycol) alkyl ether or a mixture thereof is present in the composition at a level from 0.3% to 3%. In another embodiment, the poly(alkylene glycol) alkyl ether or a mixture thereof is present in the composition at a level from 0.005% to 2%. In yet another embodiment, the poly(alkylene glycol) alkyl ether or a mixture thereof is present in the composition at a level from 0.01% to 1%. In another embodiment, the poly(alkylene glycol) alkyl ether or a mixture thereof is present in the composition at a level from 0.05% to 0.5%.

In one or more embodiments of the present invention, the composition of the present invention includes about 0.1% to about 5% of a gelling agent. Suitable gelling agents include, in a non-limiting manner, naturally-occurring polymeric materials such as locust bean gum, guar gum, sodium alginate, sodium caseinate, egg albumin, gelatin agar, carrageenin gum, sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. In one embodiment, the gelling agent is xanthan gum.

Also useful herein are gelling agents such as the acrylic acid/ethyl acrylate copolymers and the carboxyvinyl polymers sold, for example, by the B.F. Goodrich Company under the trademark of Carbopol resins. These resins include a colloidal water-soluble polyalkenyl polyether cross linked polymer of acrylic acid cross linked with from 0.75% to 2% of a cross linking agent such as polyallyl sucrose or polyallyl pentaerythritol. Examples include Carbopol 934, Carbopol 940, Carbopol 950, Carbopol 980, Carbopol 951 and Carbopol 981.

A gelling agent, for example, xanthan gum, acts as a thickener and a pseudo-plasticizer which permits the composition of the present invention to thin out under stress to flow through a spray gun. Upon making contact with the wart, the composition gels and stays in place, allowing for greater contact time and making it more resistant to runoff. Since the treatment area involves regions of cows' hoof, which by its nature is not stationary, this feature of the presently taught composition is new and useful. Such gelling agents (e.g., xanthan gum, polymeric thickeners, cellulose thickeners, propylene glycol, glycerin, or the like) in the composition allow the composition to remain in contact with the infected area of the foot for a longer period of time than a formulation without the thickener/gelling agent.

Xantham Gum would be classified as a gelling agent. It can thicken the aqueous solution and it was conceived that, with the gelling agent, one can spray once a vertical plane and the solution will cling to the surface and stick to the intended target. This is useful because the composition needs contact time (preferably at least about 4 minutes) to produce successful results. In a wet, dirty environment, a more viscous solution can adhere and keep more of the treatment solution on the target area. Xanthan gum also lowers the vapor pressure of the solution. Glutaraldehyde use at high concentrations could present potential inhalation issues to workers, and the use of gelling agents like xantham gum, and to some extent propylene glycol, acts as a carrier for the glutaraldehyde and prevents it from being atomizing into the air. In one embodiment of the present invention, this property of the final product makes the product user friendly and is beneficial and overcomes any potential problem which could exist with use of glutaraldehyde or other fixatives.

The composition of the present invention can include about 0.1% to about 1% of a gelling agent. In another embodiment, the gelling agent is present in the composition at a level from 0.03% to 3%. In another embodiment, the gelling agent is present in the composition at a level from 0.05% to 5%. In another embodiment, the gelling agent is present in the composition at a level from 5% to 15%.

In one embodiment, the composition of the present invention comprises quaternary ammonium compounds. Suitable quaternary ammonium compounds for use herein are quaternary ammonium compounds containing alkyl or substituted alkyl groups, alkyl amide and carboxylic acid groups, ether groups, unsaturated alkyl groups, and cyclic quaternary ammonium compounds, which can be chlorides, dichlorides, bromides, methylsulphates, chlorophenates, cylcohexylsulphamates or salts of the other acids. Among the possible cyclic quaternary ammonium compounds are the following: alkylpyridinium chlorides and/or sulphates, the alkyl group being preferably cetyl, dodecyl or hexadecyl group; alkylisoquinolyl chlorides and/or bromides, the alkyl group being preferably dodecyl group. Particularly suitable quaternary ammonium compounds for use herein include octyl decyl dimethyl ammonium chloride, dioctyl dimethyl ammonium chloride, didecyl dimethyl ammonium chloride, alkyl dimethyl benzyl ammonium chloride, alkyl dimethyl benzyl ammonium chloride wherein the alkyl is one or more of $C_{12}$ $C_{14}$ and $C_{16}$ alkyl, alkyl dimethyl ammonium saccharinate, cetylpyridinium and mixtures thereof.

The one or more quaternary ammonium compounds of the present invention are present in the composition at a level from 0.001% to 30%. In one embodiment, the one or more quaternary ammonium compounds of the present invention are present in the composition at a level from 0.5% to 20%. In another embodiment, the one or more quaternary ammonium compounds of the present invention are present in the composition at a level from 1% to 15%. In yet another embodiment, the one or more quaternary ammonium compounds of the present invention are present in the composition at a level from 1% to 10%. In another embodiment, the one or more quaternary ammonium compounds of the present invention are present in the composition at a level from 5% to 13%. In yet another embodiment, the one or more quaternary ammonium compounds of the present invention are present in the composition at about 10%. In yet another embodiment, the one or more quaternary ammonium compounds of the present invention are present in the composition at about 25%. In one embodiment, the one or more quaternary ammonium compounds of the present invention are present in the composition at a level from 10% to 30%.

In another aspect of the present invention, the composition includes and/or is used in combination with an effective amount of one or more surfactants. The inclusion of the surfactant in the composition can improve the performance of composition (e.g., improve wetting properties of the composition, stabilize components in the composition, function as an emulsifying agent, reduce filming and/or streaking). A variety of surfactants can be used in the composition. Such surfactants include, but are not limited to, nonionic, semipolar, anionic, cationic, zwitterionic, and/or amphoteric surfactants. Many of these surfactants are described in McCutcheon's Emulsifiers and Detergents (1997), Kirk-Othmer, Encyclopedia of Chemical Technology, 3rd Ed., Volume 22, pp. 332-432 (Marcel-Dekker, 1983), and McCutcheon's Soaps and Detergents (N. Amer. 1984), the contents of which are hereby incorporated by reference. Typically the surfactant is partially or fully soluble in water.

In one embodiment, the surfactant includes, but is not limited to, glycoside, glycols, ethylene oxide and mixed ethylene oxide/propylene oxide adducts of alkylphenols, the ethylene oxide and mixed ethylene oxide/propylene oxide adducts of long chain alcohols or of fatty acids, mixed ethylene oxide/propylene oxide block copolymers, esters of fatty acids and hydrophilic alcohols, sorbitan monooleates, alkanolamides, soaps, alkylbenzene sulfonates, olefin sulfonates, paraffin sulfonates, propionic acid derivatives, alcohol and alcohol ether sulfates, phosphate esters, amines, amine oxides, alkyl sulfates, alkyl ether sulfates, sarcosinates, sulfoacetates, sulfosuccinates, cocoamphocarboxy glycinate, salts of higher acyl esters of isethionic acid, salts of higher acyl derivatives of taurine or methyltaurine, phenol poly ether sulfates, higher acyl derivatives of glycine and methylglycine, alkyl aryl polyether alcohols, salts of higher alkyl substituted imadazolinium dicarboxylic acids, ferchorics, tannics, naphthosulfonates, monochloracetics anthraflavinics, hippurics, anthranilics, naphthoics, phthalics, carboxylic acid salts, acrylic acids, phosphates, alkylamine ethoxylates, ethylenediamine alkoxylates, betaines, sulfobetaines, and/or imidazolines.

In one aspect of this embodiment, the surfactant includes, but is not limited to, lauryl sulfate, laurylether sulfate, cocamidopropylbetaine, alkyl polyglycosides, and/or amine oxides. In one embodiment, the surfactant is selected from the group consisting of polyoxyethylene alcohols, alkyl ether sulfates, and alkyl sulfates. In one embodiment, the surfactant is an ethoxylated nonylphenol. CO 720 ethoxylated nonylphenol, for example, helps unwind the protein fibers, allowing them to be available for cross-linking. The CO 720 ethoxylated nonylphenol also acts as an emulsifier for the methyl salicylate. Ethoxylated nonylphenol is a polyether. In another embodiment, the present aqueous solution/composition of the present invention comprises one or more polyethers.

CO 720 (ethodylated nonyl phenol) is a surface-active agent that would be considered a surfactant. It prepares the surface to be treated so that a fixing agent like glutaraldehyde can achieve greater penetration. This helps condition the surface by unwinding the tightly bound proteins so that the glutaraldehyde or another cross-linking agent, for example another di-aldehyde, can then crosslink using their two aldehyde groups. QUATS, quaternary ammonium compound, may also act as surfactants and work in the same way when used in combination with a fixing agent like glutaraldehyde. Bactericidal and fungicidal activities are due to the combination of glutaraldehyde with metabolic enzymes and with the amino-acids. Being hydrophilic, glutaraldehyde cannot easily cross the cell's lipid membrane.

The one or more surfactants of the present invention are present in the composition at a level from 0.01% to 10%. In one embodiment, the one or more surfactants of the present invention are present in the composition at a level from 0.5% to 5%. In another embodiment, the one or more surfactants of the present invention are present in the composition at a level from 1% to 4%.

One aspect of the present invention is directed to a copper-free and zinc-free composition for the treatment and/or prevention of one or more infectious diseases of the hoof in animals, comprising at least one cross-linking agent, wherein said cross-linking agent is not formaldehyde. In one embodiment, the composition comprises about 5% to about 30% by weight of at least one cross-linking agent; about 5% to 20% by weight of at least one quaternary ammonium compound; about 0.03% to 3% by weight of at least one apoly(alkylene glycol) alkyl ether; about 0.03% to 3% by weight of at least one gelling agent; about 0.03% to 3% by weight of at least one antimicrobial essential oil or active thereof; and about 0.03% to 5% by weight of at least one surfactant.

One aspect of the present invention is directed to a composition for the treatment and/or prevention of one or more infectious diseases of the hoof in animals, comprising one or more cross-linking agents; one or more quaternary ammonium compounds; one or more gelling agents; one or more surfactants; one or more antimicrobial essential oils or actives thereof; and one or more poly(alkylene glycol) alkyl ethers.

One aspect of the present invention is directed to a method for treating and/or preventing papilomatous digital dermatitis in an ungulate, comprising: preparing a copper-free and zinc-free composition comprising at least one cross-linking agent and at least one quaternary ammonium compound; and spraying or applying in a foam a therapeutically effective amount of said composition to a lower leg and hoof area of said ungulate in order to treat and/or prevent said papillomatous digitial dermatitis.

In another aspect of the present invention, the composition includes and/or is used in combination with one or more biocides. Such biocides can include, but are not limited to, alcohols, peroxides, boric acid and borates, chlorinated hydrocarbons, organometallics, halogen-releasing compounds, mercury compounds, metallic salts, pine oil, organic sulfur compounds, iodine compounds, silver nitrate, quaternary phosphate compounds, and/or phenolics.

In one embodiment of the present invention the compositions may further comprise a pH buffer i.e. a system composed of a compound or a combination of compounds, whose pH changes only slightly when a strong acid or base is added. Suitable pH buffers and amount to use are known to those skilled in the art. For example, suitable organic acids for use herein include monocarboxylic acids, dicarboxylic acids and tricarboxylic acids, acetic acid, citric acid, malonic acid, maleic acid, malic acid, lactic acid, glutaric acid, glutamic acid, aspartic acid, methyl succinic acid, succinic acid or mixtures thereof. In one embodiment, the citric acid and succinic acid or mixtures thereof are used.

The composition can be used at a range of effective concentrations. In some embodiments, the composition has a pH of about 1.0 to about 6.0. In other embodiments, the composition has a pH of about 1.0, about 1.5, about 2.0, about 2.5, about 3.0, about 3.5, about 4.0, about 4.5, about 5.0, about 5.5, or about 6.0.

The compositions described herein can be contacted with an animal foot/hoof in an amount effective to result in a reduction significantly greater than is achieved by washing with water, or at least a 50% reduction, at least a 90% reduction, preferably at least a 99% reduction, in the resident microbial preparation.

The present methods usually require a certain minimal contact time of the composition with the foot/hoof of an animal for the treatment and/or prevention specified. The contact time can vary with concentration of the use composition, method of applying the use composition, temperature of the use composition, amount of soil and/or contamination on the hoof, number of microorganisms present on the hoof, type and formulation of the disinfection composition, or the like.

The minimum exposure time to the presently taught composition is, for example, at least about 2 to about 5 seconds. The exposure time can be, for example, at least about 15 seconds, at least about 30 seconds, at least about 45 seconds, at least about one minute, at least about two minutes, at least about three minutes, at least about four minutes, at least about five minutes, at least about six minutes, at least about seven minutes, at least about eight minutes, at least about nine minutes, at least about ten minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, or at least about 60 minutes. In one embodiment, the exposure time to the presently taught composition is between about 5 to about 30 minutes. In one embodiment, the exposure time to the presently taught composition is between about 5 to about 120 minutes. Even longer exposure times are contemplated, for example, several hours or even days. After direct exposure during administration, it is contemplated that the disinfection composition can remain in contact with a hoof for extended periods of time. Generally, longer exposure times to the disinfection composition will be preferred as the pH increases.

Application of the composition to an animal's foot can occur in periodic applications. An effective amount of the composition can be applied to an animal's foot several times per day and/or several times over a period of several days. For example, the composition can be applied to part or all of an animal's foot/hoof about every one hour, about every two hours, about every three hours, about every four hours, about every five hours, about every six hours, about every seven hours, about every eight hours, about every nine hours, about every ten hours, about every eleven hours, or about every twelve hours. Longer periods of time between applications are contemplated. For example, the composition may be applied every day, every other day, every three days, or every several days. In general, application of the present composition once or twice on the same day or consecutive days has an effect.

It is contemplated that the presently taught composition can be administered in the same or different form as a single dose or in multiple applications. In some embodiments, a first composition and a second antimicrobial composition are applied serially to the foot of an animal. In some embodiments, a first concentrated composition is diluted with water to form a first antimicrobial composition, and a second concentrated composition is diluted with water to form a second antimicrobial composition. The first and the second antimicrobial composition can be applied serially or jointly to a foot of an animal at predetermined intervals. In some embodiments, the method for treating a foot of an animal comprises contacting a foot of an animal with any of the compositions taught herein. The compositions of the application can be diluted in water to prepare for use. In one embodiment, the composition is diluted between about 10-fold to about 400-fold in water before treating the foot of the animal. In an embodiment, the composition is diluted about 200-fold in water.

The composition may comprise additional components, including for example skin conditioners, such as glycerin, propylene glycol, sorbitol, lanolin, derivates of polyethylene glycol (PEG)-lanolin and polypropylene glycol (PPG)-lanolin, aloe vera, and allantoin, to promote skin health and healing. Buffering agents may be used to adjust pH. Buffers may include organic acids, such as monocarboxylates, phosophoric acid, carbonates, and similar products. The pH may be adjusted by adding alkalinity such as sodium bicarbonate, sodium carbonate, sodium hydroxide and potassium hydroxide. Film forming polymers may be used, including polyethylene glycol resins, polyvinyl alcohol, polyacrylates, polyvinyl pyrrolidinone, polyurethanes and corresponding copolymers.

The composition may also comprise antimicrobial agents such as quat based antimicrobials, phenolics, peracids, hydrogen peroxide, acidified sodium chlorite, hypochlorous acid, iodine, chlorhexidine, aldehyde-based germicides, and fatty acids. Colorants selected from generally recognized dyes and pigments may also be part of the composition. Any of these components may be used in various combinations depending on the desired features of a particular product.

The compositions and methods described herein, used alone or in combination with other known treatment compositions and modalities, can be directed to the treatment and/or prevention of an infectious disease of the foot of an animal. The compositions and methods of the present invention have activity against a wide variety of microorganisms such as Gram positive and Gram negative bacteria, yeast, molds, bacterial spores, and viruses. Treatments with any of the compositions of the present invention can be applied one time or repeatedly within a short period of time (minutes or hours), or the treatments can be repeated as needed over a longer period of time (days or months).

One aspect of the invention is directed towards treatment and/or prevention of one or more infectious diseases of a foot of an animal by administration of the compositions described herein. Infectious diseases of the foot of an animal that can be treated and/or prevented with compositions and methods described herein include, but are not limited to hairy heel warts, foot rot, and/or scald (foot rot includes, but is not limited to, stable foot rot) or other conditions caused by *Fusobacterium necrophorum, Bacteroides melaminogenicus*, and/or *Diechelobacter nodosus*. The term animal includes cattle, and thus both cows and steers, as well as other animals and mammals.

In various embodiments, the animal to be treated is an ungulate. In one embodiment, the subject of various treatments described herein is a cow, a sheep, a horse, or a goat. In another embodiment, the ungulate to be treated with the composition of the present invention is a cow. Infectious diseases in the hooves of cows are most prevalent in dairy cow herds but are also problematic in beef cattle. The treatment compositions and methodologies described herein can be directed to dairy and/or beef cattle. In some embodiments, the ungulate to be treated with a composition of the present invention is a goat. In some embodiments, the ungulate to be treated with the composition of the present invention is a horse. In other embodiments, the ungulate to be treated with an antimicrobial composition of the present invention is a sheep.

An animal foot can be contacted with a composition described herein by any method or apparatus suitable for applying the presently taught composition. For example, although extensive studies were performed using spray and foam formulations, it is contemplated that the presently taught composition may be administered by other means known to those skilled in the art. Various embodiments provides for components of the footbath, spray, gel or foam form of the composition to be administered sequentially. In other embodiments of the present invention, a footbath, spray, gel or foam form of the composition can be administered sequentially with an antimicrobial composition in the same or another form such as a footbath, powder, spray, gel, or foam.

As stated supra, the solution described herein is specifically formulated to be applied to the hooves and lower legs of the animal as a spray or foam formulation. Labor costs are a major concern to farmers. In one embodiment, an automated system is used to apply the solution, in order to reduce labor costs. The automated system may use a programmable time sequence and/or sensors that trigger dispensing. For example, in a spray application, sensors may be used to determine a presence of an animal requiring treatment.

In one embodiment, it is contemplated that other means of applying the solution as taught herein may achieve results that improve upon existing methods of treating one or more diseases of the foot of an animal. For example, the taught solution herein may be used in a foot bath application, whether a traditional liquid solution or a foam, and a program may be used such that the treatment is dispensed into the trough at specific time intervals, and the old treatment solution is automatically drained before dispensing the replacement treatment solution. Instead of a time interval, the system may monitor a number of animals that have passed through the trough and automatically replenish the trough at a predetermined interval. Alternatively, sensors within the trough may be used to determine when the solution falls below a predetermined concentration (due to contamination in the trough) and/or when waste levels in the trough reach a specific level.

In another embodiment, the use of absorptive pads saturated with the composition may be used for treatment, however, wrapping with pads should be loose. Generally, wrapping will prevent the formation of a scab, the rapid formation of which is facilitated by the presently taught methods and compositions, and which is necessary for healing.

For dairy cows, the treatment can be applied prior to entering a milking parlor. Milking parlors are generally kept very clean, thus providing adequate time for contact between the solution and the skin and the hoof before returning to a potentially soiled environment. Alternatively, the treatment may be applied as the cows exit the milking parlor such that the cows receive the treatment immediately prior to moving to a housing environment that may be dirty. The composition may be applied periodically, such as every day, every other day, or once a week. Generally, one or two applications either on same day or on consecutive days facilitates formation of a scab.

In some embodiments, more than one application technique may be used in combination or multiple applications may be used. For example, a spray followed by foam may be used in series, or a foot bath followed by a spray or foam administration. The first foot bath may contain a detergent solution to remove dirt and manure from the hooves; the second spraying or foaming containing the solution as taught herein. In another aspect of the invention, a rotation of treatments may be used. In one embodiment of the present invention, the affected area is first cleaned, for example washed with water or by a first pass through a footbath, to clear the mud and manure for example and provide good exposure of the lesion to the to-be administered composition of the present invention.

6.3 Formulations

The present invention includes any known application technique for delivering an composition to the lower leg and hoof of the animal. The applications include, but are not limited to, foam, direct spraying, and propellant spray. In one embodiment, an automated system, as described further below, is used for applying the composition to the animals.

Foot baths are currently the most common application mode for treating hairy heel warts and other hoof related diseases. Cows are directed to walk through troughs containing the liquid treatment. A disadvantage of foot baths is that the liquid treatment may easily become contaminated due to organic waste from the cows. In some cases the foot bath may even become a vehicle for transferring bacteria to other cows. Foot baths thus may require frequent replenishment, as well as significant labor commitments in some cases.

6.3.1. Spray

As an alternative to a foot bath, the composition may be sprayed on the hooves. An advantage of a spray application is that a fresh treatment is applied to each cow, as compared to a foot bath application which may become contaminated over time. In some embodiments, a worker may individually spray each cow as the cow is on its way into or out of the milking parlor. Alternatively, an automated system may be used to spray the treatment onto the hooves.

In various embodiments, the compositions described herein can be administered as a spray. In one embodiment, the presently taught compositions are sprayed onto the lesion so as to adequately cover the lesion. Depending on the lesion size, this can take about 3 ml to about 10 ml of the composition being sprayed onto the lesion. The compositions can be applied using fixed or articulating nozzles, at higher pressures, varying or steady flow rates, various temperatures, and/or with or without agitation or brushes. Spraying can be accomplished by an apparatus such as a spray cabinet with stationary or moving spray nozzles. The nozzles can create a mist, vapor, or spray that contacts an animal's feet. The spray can be set up as a walk-through pen or in a holding pen. In one embodiment, the composition as taught herein is applied either with the 32 oz hand pump sprayer or a larger pump sprayer. In one embodiment, the composition is a thinner formulation used to spray either the entire herd or individual warts, named HealMax Herd Spray.

Application of a material by spray can be accomplished, for example, using a manual spray wand application, an automatic spray of the animals moving through a gate or room or gateway, or the like. Multiple spray heads to ensure complete contact or other spray means may be used. In one embodiment, an automatic spray application is used, involving the use of a spray booth. The spray booth substantially confines the sprayed composition to within the parameter of the booth. The spray booth can include steam jets that can be used to apply the compositions of the present invention. The spray pattern can be virtually any useful spray pattern.

When using a spray application, additional components may be included in the composition to enhance application of the solution onto the skin and hooves. In some embodiments, thickeners may be used to retain a greater quantity of liquid per skin area. Surfactants may also be used in combination with or as an alternative to thickeners. The surfactants reduce the surface tension of the aqueous composition on the skin and thus help the solution to wet and spread over the skin. The composition also may contain film forming polymers that dry to a second skin to help in holding the composition to the skin or to provide a protective barrier to the skin.

In some embodiments, a thickener is used in a spray application to increase a viscosity of the composition. In other embodiments, the viscosity of the composition is equal to or greater than approximately 20 centipoise for spray applications. Suitable thickeners may include polymeric thickeners, clays, silicas, and associative thickeners. Moreover, surfactant thickened systems may be used to form an composition having the desired viscosity for spraying the composition onto the hooves and lower legs of an animal. A propellant spray also may be used to apply a composition to the hooves and lower leg area. The propellant spray typically requires the use of volatile propellants.

6.3.2. Other

In additional embodiments, the composition taught herein may be applied as a foam. The foam may be applied in two ways. The foam may be dispensed into a trough and the cows may then walk through the foam, similar to a liquid foot bath. Alternatively, the foam may be applied directly to the hooves using any known foam dispensing technique. In one embodiment, where a flash foamer is added to this spray, the product may effectively be foamed onto warts, with the use of a foam sprayer. The presently taught foam composition, named HealMax Foam, is an effective treatment method because, inter alia, the foam provides improved accuracy and the foam increases contact/treatment time.

The foam can be prepared, for example, by mixing foaming surfactants with the composition. The foaming surfactants can be nonionic, anionic, or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines, and alkyl amides. The foaming surfactant is typically mixed at time of use with the composition but can be prepared in advance of the time of use. At time of use, compressed air can be injected into the mixture, and the foam can be applied to a foot of an animal.

Thickeners (e.g., xanthan gum, polymeric thickeners, cellulose thickeners, propylene glycol, glycerin, or the like) can be further combined to produce a foam which may remain in contact with the infected area of the foot for a longer period of time than a formulation without the thickener. In some embodiments, a foam antimicrobial composition contains about 5 wt % to about 20 wt % of one or more thickeners. In a foam application, two important parameters include the density of the foam (i.e. how much liquid per unit volume) and the stability of the foam (specifically, a drainage rate of the foam). In one embodiment, the foam is intrinsically viscous and allows greater foam stability. For foam applications, an appropriate viscosity range for the composition is between approximately 14 and 100 centipoise. Many of the same features that beneficial to a spray application may also be useful in a foam application. For example, surfactants and thickeners may both be used to improve foam properties.

The foamed composition, according to one or more embodiments of the present invention, is of exceptionally low specific gravity, for example, the foamed composition has a specific gravity in the range of about 0.02 gr/ml to about 0.35 gr/ml. Although of low specific gravity, the foam is highly stable and will remain without collapse for several minutes. Nonetheless, the foam collapses readily upon application of mild shear stress. Low specific gravity, high foam stability and ready collapsibility all contribute to a foamed composition that is easily applied and administered over large areas without rubbing or chaffing of the affected area. A foam adjuvant is included in the composition to improve the stability and reduce the specific gravity of the foamed composition. In one or more embodiments of the present invention, foam adjuvants include fatty alcohols, fatty acids, and mixtures thereof. The foam adjuvant can include at least one fatty alcohol and at least one fatty acid.

The foamed composition, according to one or more embodiments of the present invention, is dispensed from a glass or plastic container that dispenses foam in the absence of a gas or liquid propellant. Alternatively, the composition of the present invention further includes a liquefied or compressed gas propellant at a concentration of about 3% to about 25% of the total composition. Examples of suitable propellants include volatile hydrocarbons such as butane, propane, isobutane or mixtures thereof, and fluorocarbon gases. In another embodiment, the composition according to one or more embodiments of the present invention is preferably placed, together with a liquefied or compressed gas propellant in the amount of about 3% to about 25% of the total composition, in an aerosol container. Upon pressing the actuator, a breakable foam, suitable for topical administration is released.

In other embodiments, the composition can be administered as a gel. The animal's foot can be treated with a thickened or gelled version of the composition. In the thickened or gelled state, the composition can remain in contact with the animal's foot for longer periods of time, thus increasing the antimicrobial efficacy. The thickened or gelled solution can also better adhere to vertical surfaces and crevices in the animal's foot. The composition can be thickened or gelled using one or more thickening agents including, but not limited to, xanthan gum, polymeric thickeners, cellulose thickeners, propylene glycol, glycerin, or the like. The thickeners or gel forming agents can be used, for example, in the concentrated product or by mixing with the antimicrobial composition at time of use. Exemplary use levels of thickeners or gel agents can range from about 100 ppm to about 10%, by weight.

In one embodiment, a footbath is used Immersing an animal's foot in the aqueous solution of the present invention can be accomplished by any of a variety of methods known to those of skill in the art. For example, troughs can be used to immerse the feet. The composition of the present invention, contained in the trough, can be agitated so as to increase the application and/or absorption of the solution into or onto the feet. Agitation can be obtained by conventional methods, including ultrasonics, aeration by bubbling air through the solution, by mechanical methods, such as strainers, paddles, brushes, pump driven liquid jets, or by combinations of these methods. The composition can be heated to increase the efficacy of the solution in killing microorganisms. After the foot has been immersed for a time sufficient for the desired effect, the foot can be removed from the bath and the antimicrobial composition can be rinsed, drained, blotted, or evaporated from the foot. Treatments with any of the compositions of the present invention can be applied one time or repeatedly within a short period of time (minutes or hours), or the treatments can be repeated as needed over a longer period of time (days or months).

6.4 Kits

In various embodiments, the present invention can also involve kits for use in the treatment of an infectious disease of a foot of an animal. Such kits can include the presently taught compositions and, in certain embodiments, instructions for administering and/or using the composition. When supplied as a kit, the different components of the composition can be packaged in separate containers and admixed immediately before or during use. Such packaging of the components separately can, if desired, be presented in a pack or dispenser device which may contain one or more unit dosage forms containing the composition. Such packaging of the components separately can also, in certain instances, permit long-term storage without losing activity of the components. In various embodiments, the different components can be packaged in one composition for administration together.

In certain embodiments, the concentrates may be sold as a kit, which includes instructions for mixing the concentrates to form a composition with appropriate properties. Instructions may be printed on paper or other substrate, and/or may be supplied as an electronic-readable medium. Detailed instructions may not be physically associated with the kit; instead, a user may be directed to an internet web site specified by the manufacturer or distributor of the kit. As an example, the instructions may include instructions for forming a solution having a specific concentration and/or instructions to adjust a pH level of the composition.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

7. EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

7.1 Example 1

HealMax Wart Spray I Development and Field Testing

|  | HealMax Wart Spray I (%) | HealMax Herd Spray (%) |
| --- | --- | --- |
| Glutaraldehyde 50% | 25 | 25 |
| Deionized Water | 69.34 | 69.68 |
| C.O. 720 (ethoxylated nonyl phenol) | 2.60 | 2.60 |
| Methyl Salicylate | 1.35 | 1.35 |
| Propylene Glycol | 1.35 | 1.35 |
| Xanthan Gum | 0.34 | — |
| Green Dye | 0.02 | 0.02 |

A trial was conducted on a 500 cow commercial Holstein dairy in Hanford, Calif. (Fragosa & Sons) which was experiencing a rapid outbreak of digital dermatitis. Dairy had been using an acidified copper sulfate footbath once a day for 4-5 days per week. 10% of dairy cows (50) showed signs of clinical lameness due to advanced digital dermatitis lesions. A qualified hoof trimmer, using a trimming chute, inspected and selected 5 cows with visible lesions due to digital dermatitis. These cows were not allowed to pass through the regular footbath during the 4 day trial period.

| Lesion Severity: The severity of each lesion was scored as follows: | |
| --- | --- |
| 0 | No visible lesion. |
| 1 | Early Stage: Skin slightly broken, redness, inflammation. |
| 2 | Moderate Stage: Visible open lesion, redness, inflammation, some blood. |
| 3 | Advanced Stage: Visible open lesion, redness, inflammation, very bloody. |
| Lameness: Each cows locomotion was observed and assigned a lameness score as follows: | |
| 0 | No visible lameness |
| 1 | Slight Lameness. Noticeable while walking. |
| 2 | Moderate/Severe Lameness. Difficulty walking, visibly lifting leg to reduce weight. |

A control group of 5 cows was chosen and ranked according to the same criteria as the test group. This group was allowed to walk through the regular daily footbath treatment consisting of acidified copper sulfate. Cows were milked three times per day and the foot bath was operated for one milking per day.

Each treatment of HealMax Herd Spray was applied while the cow was immobilized in a trimming chute. Each lesion was cleaned of debris with water, photographed, and then sprayed with enough of the presently taught composition to completely cover the lesion. Treatment dosage averaged 4-6 spays or 4-6 ml of product. In one embodiment, it is conceived that about 10 ml to about 20 ml of the composition is administered by spray or foam to the hoof. Each cow was then given 5 minutes to lay idle before being released from the trimming chute.

After 4 days both the test group and control group were sequestered from the herd and examined by the same hoof trimmer while on the trimming chute. Each lesion was then ranked to determine the treatment effect according to the following criteria:

| | |
|---|---|
| (−2) | Lesion significantly increased in size and severity. Additional Treatment Required. |
| (−1) | Lesion increased in size and severity. Additional Treatment Required. |
| (0) | No visible signs of improvement. Lesion stayed about the same size and severity. Additional Treatment Required. |
| (+1) | Lesion shows slight signs of improvement. Some white scabbing. Redness and/or visible blood. Additional Treatment Required. |
| (+2) | Lesion shows significant signs of improvement. White and/or black scab formation. Some redness visible. Additional Treatment Optional. |
| (+3) | Lesion shows dramatic signs of improvement. White and/or black scab. No additional treatment required. |

Post treatment lesion severity was observed and ranked according to the initial criteria:

| | |
|---|---|
| 0 | No visible open lesion. |
| 1 | Early Stage: Skin slightly broken, redness, inflammation. |
| 2 | Moderate Stage: Visible open lesion, redness, inflammation, some blood. |
| 3 | Advanced Stage: Visible open lesion, redness, inflammation, very bloody. |

Test Group—showed a significant improvement in all test cows that were treated with the presently taught composition (see FIG. 5 and table below). After about five days, the warts were mostly healed and the animals were able to walk and feed normally. Administration of the presently taught spray composition created darkened waterproof scabs, which sealed off the open warts. 4 out of 5 cows required no further treatment due to complete and thorough scabbing of lesions. Only Cow 251 which had a severe lesion prior to treatment required one additional treatment. Lameness post treatment decreased for each cow. Application of a second spray after one or two days of the first spray application showed great effect on severely affected animals.

Control Group (Acidified Copper Sulfate Footbath)—Lesions either increased in severity or stayed the same with no perceptible difference. Lesions with an initial severity rating of 2 or 3 tended to increase in severity while lesions with an initial severity rating of rated 1 or 2 stayed about the same or slightly increased in severity. Lameness post treatment either stayed the same or increased. This result was consistent with copper sulfate footbaths during an outbreak of digital dermatitis. Typically, larger and severe warts tend to get worse, while smaller less established warts either get worse or stay the same.

| Cow # | Severity - Initial | Lameness | Treatment Effect | Severity - Post Treatment | Lameness - Post |
|---|---|---|---|---|---|
| Test Group HealMax Wart Spray, 1 application | | | | | |
| 89 | 3 | 2 | (+3) | 0 | 0 |
| 251 | 3 | 2 | (+2) | 1 | 1 |
| 667 | 3 | 2 | (+3) | 0 | 0 |
| 524 | 2 | 2 | (+3) | 0 | 0 |
| 72 | 2 | 1 | (+3) | 0 | 0 |
| Control Group Acidified Copper Sulfate, once per day, 4 days | | | | | |
| 376 | 2 | 1 | (−2) | 3 | 2 |
| 492 | 3 | 2 | (−1) | 3 | 2 |
| 27 | 3 | 2 | (−1) | 3 | 2 |
| 399 | 2 | 1 | 0 | 2 | 1 |
| 602 | 1 | 1 | 0 | 1 | 1 |

7.2. Example 2

Cross-Linking Tests and Development of Healmax Wart Spray II

| Components | HealMax Wart Spray II (%) |
|---|---|
| Glutaraldehyde 50% | 8.3 |
| Glyoxal 40% | 16.66 |
| C.O. 720 (ethoxylated nonyl phenol) | 2.60 |
| Methyl Salicylate | 1.35 |
| Propylene Glycol | 1.35 |
| Polymer gum | 0.50 |
| QUAT BTC855 | 10.00 |
| Deionized Water | Balance |

Additional experiments were conducted in order to further develop a product, optionally using substantially less glutaraldehyde, but with the same or better performance than the presently taught novel HealMax Wart Spray I. It was conceived that such a novel composition for the prevention and/or treatment of one or more infectious diseases of the hoof in animals could be formulated by using less glutaraldehyde in order to reduce the cost and any other potential issue associated with use of higher concentrations of glutaraldehyde. The components used were Glutaraldehyde (Dow, BASF), CO720 (Rhodia, Huntsman), methyl salicylate (Polarome), propylene glycol (Dow), xanthan gum (AEP Colloids) and green dye (Sensient by Prime Ingredients).

Figure 2:
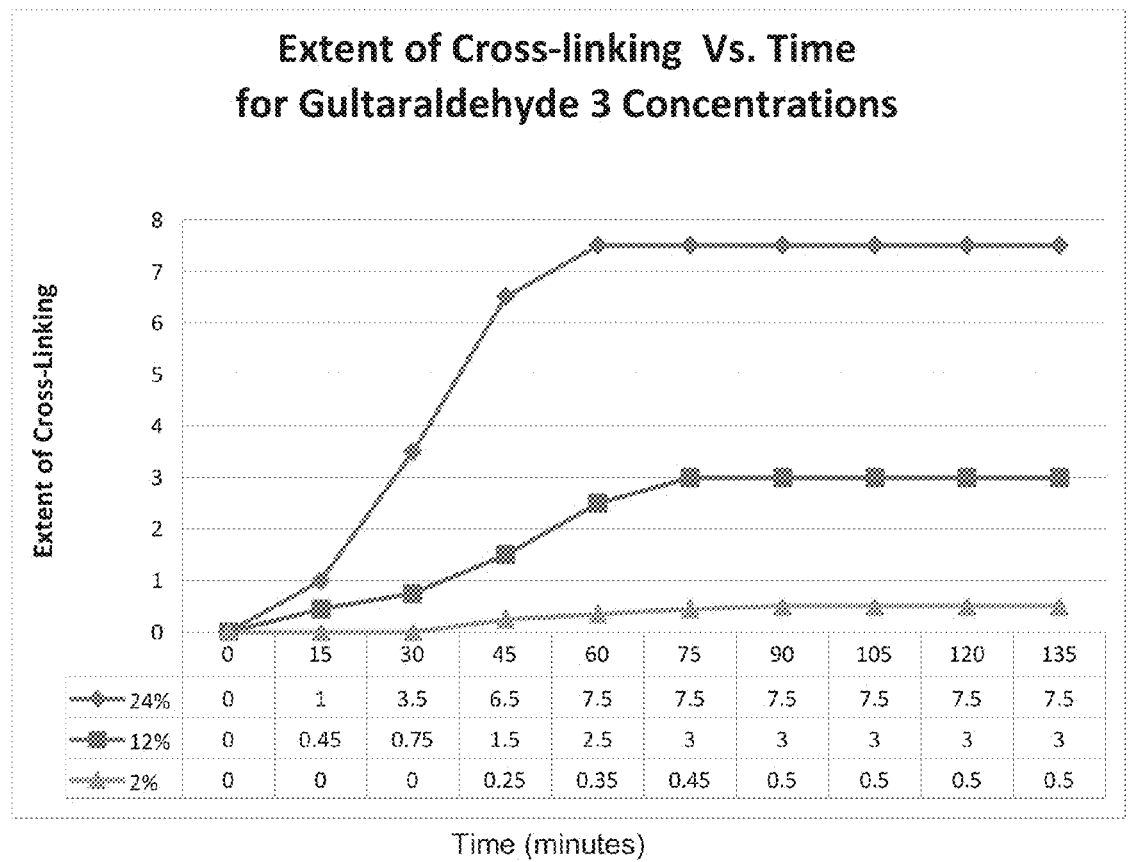
FIG. 2 is a line graph showing the extent of cross-linking of the protein medium over time where three dilutions of glutaraldehyde 50% was used.

By reducing the amount of glutaraldehyde to less than 5% resulted in significantly less cross-linking of test samples (see FIG. 2). Furthermore, actual application of such a low concentration of glutaraldehyde on digital dermatitis lesions showed that the concentration was ineffective at facilitating adequate scab formation in an acceptable time span. Unlike fixation of microscopy samples or sterilization of instruments using glutaraldehyde, there is a limited amount of time on a dairy farm in which to achieve acceptable results. This time generally corresponds with 5-10 minutes that milking cows spend in the relatively clean environment of a milking parlor for example. After that time period, cows are released into a significantly dirtier and often wetter environment where they quickly step in a mud, manure, urine, and water mixture known as "Slurry". Therefore, rapid formation of the scab is necessary. In one embodiment of the present invention, after spraying or foaming of the presently taught composition, a scab forms within about five to about fifteen minutes.

Several di-aldehydes with properties similar to glutaraldehyde were considered for their ability to cross-link samples. Glyoxal was selected because it is the smallest di-aldehyde molecule and it was conceived that this would provide a desired efficacy in the context of germicidal (cross-linking) ability. Glyoxal has bactericidal properties comparable with those of glutaraldehyde and is also used as a bactericide in preparation with other components. The bifunctionality of glyoxal is used to cross-link functionalized macromolecules such as cellulose, polyacrylamides, polyvinyl alcohol, keratin and other polycondensates. Results on biodegradation are available, showing that glyoxal is clearly readily biodegradable. In one embodiment of the present invention, the composition as taught herein is a biodegradable product.

Figure 3:
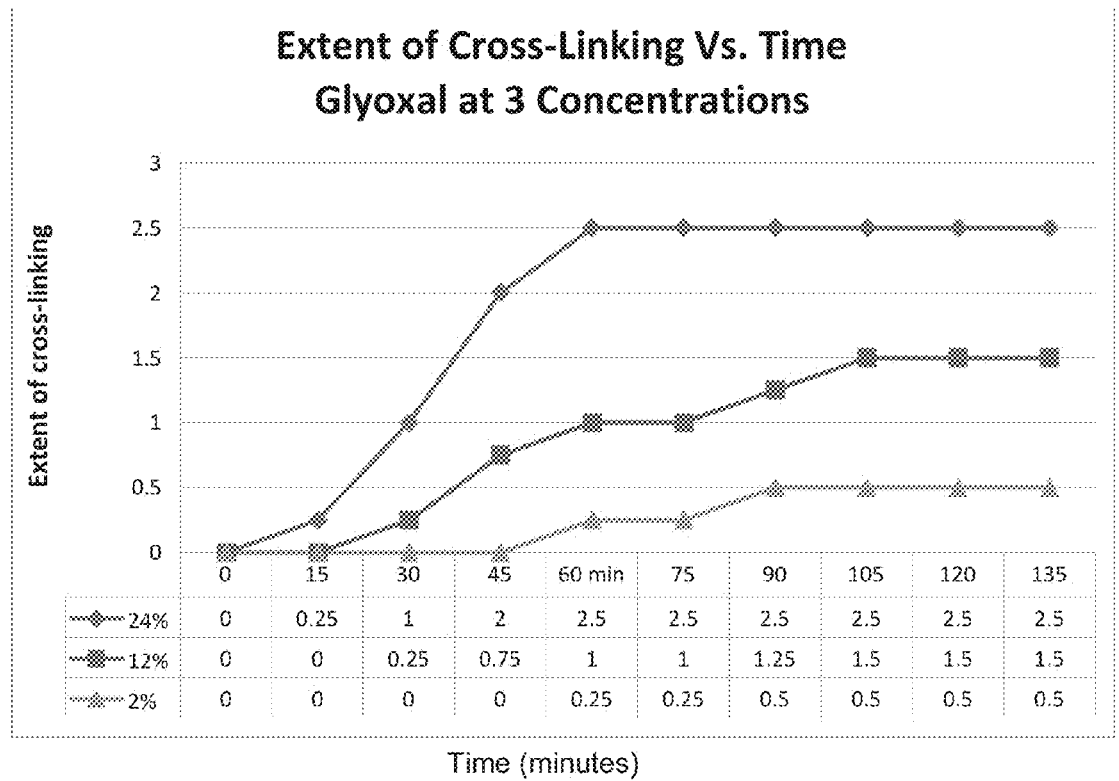
FIG. 3 is a line graph showing the extent of cross-linking of the protein medium over time where three dilutions of glyoxal 40% was used.
Figure 4:
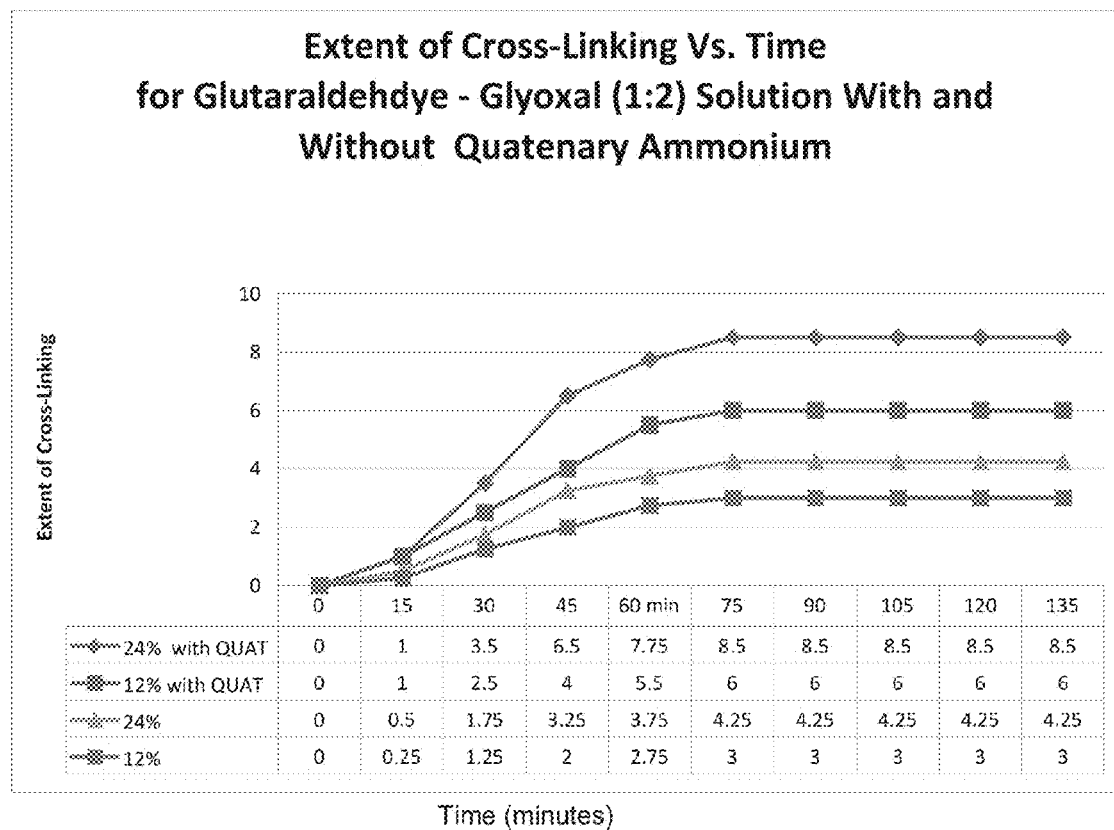
FIG. 4 is a line graph showing the extent of cross-linking of the protein medium over time where two dilutions of a mixture of glutaraldehyde 50% and glyoxal 40% at a 1:2 ratio was used, with or without a quaternary ammonium compound, QUAT at 10%.
Figure 5A:
FIG. 5 depicts results from the filed testing studies of cows affected by hairy heel warts, showing the lesion sites before and after treatment via spray of the presently taught composition.
Figure 5A:
Figure 5A:
Figure 5B:
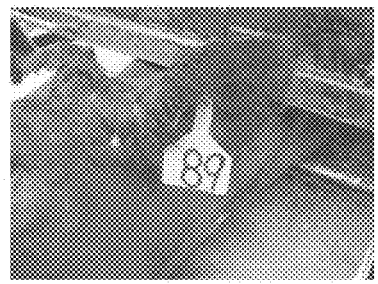
Figure 5B:
Figure 5B:
Figure 5C:
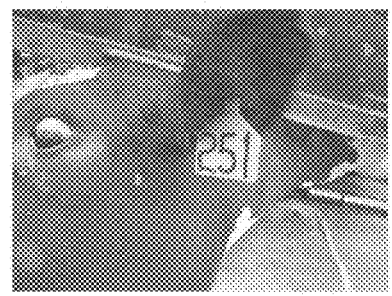
Figure 5C:
Figure 5C:

Given these characteristics, glyxol was chosen as a suitable replacement and testing commenced with glyoxal as a sole substitute. As shown on FIG. 3, glyoxal alone did produce cross-linking effects, however, at a low level (2.5 maximum). Next, it was conceived that a 2:1 ratio of glyoxal-glutaraldehyde would be effective when compared to either component alone. A quaternary ammonium compound, QUAT, was also tested with the 2:1 ratio of glyoxal-glutaraldehyde. It was surprisingly found that the combination of the 2:1 ratio of glyoxal-glutaraldehyde coupled with QUAT at 10% achieved highly desirable results as seen on the graph (see FIG. 4). This novel composition achieved a high degree and rapid rate of cross-linking, as indicated in FIG. 4. Further testing in the field showed that this new composition effectively facilitates scabbing and effectiveness similar to that of HealMax Wart Spray I.

Tests were performed in order to obtain a skin (crust) on the protein medium by using a cross-linking agent. Time, temperature and skim formation were monitored. Tests were performed at 40° F.—both medium and solutions were cooled to test temperature. Test medium was prepared by mixing a solution containing 85% D.I. water and 15% Hydrolyzed Bovine Dry Collagen (purchased from Milligan & Higgens). Approx 4 oz of the preparation was put into Petri dishes, placed in a refrigerator for thirty minutes before reacclimatizing at room temperature, ready for testing. Subsequently, the various test solutions were poured into 4 oz bottles with spray nozzles and 10 ml of solution was sprayed onto the medium in the petri dishes from a distance of 6 inches, timed and viewed at 15 minute intervals and the contents of the petri dish was then scored for skin formation. The time and extent of skin formation was noted and transposed to graphs (see FIGS. 1-4).

A second series of tests were run using Egg Albumin Powder (purchased from J. T. Baker) as the protein medium, prepared by mixing 85% D.I. water and 15% Egg Albumin Powder. Both test produced identical results.

Lab testing was performed to assess cross-linking ability of various compositions. Various cross-linkers were tested, including formaldehyde (see FIG. 1), glutaraldehyde (see FIG. 2), glyoxal (see FIG. 3), and a unique combination of components (see FIG. 4). Varying percentages of glutaraldehyde, formaldelhyde, glyoxal and the combination of components were sprayed onto the test medium in Petri dishes and compared at fifteen minute time intervals. The total test time was two to three hours.

The amount of xanthan gum to be added was determined by testing various percentages of gum sprayed through a hand spray gun. HealMax Wart Spray was sprayed onto a vertical surface and the degree of cling and run was measured. Various temperatures were tested between 40 and 90 degrees F. in order to be sure that temperature did not affect the spraying ability.

The scoring for the skin formation was as follows:

| Extent of skin formation (Scored from 0 to 10) | Properties of protein medium |
| --- | --- |
| 0-2 | very watery, lack of visible skin formation, unchanged color |
| 3-4 | very thin skin formation, slight pale yellow color change |
| 5-6 | thin to moderate skin formation, pale to light yellow color change |
| 7-8 | firm skin, approx 2-3 mm thickness, medium yellow color |
| 9-10 | very firm skin, approx 3 mm thick, medium to dark yellow color |

7.3 Example 3

Field Testing

HealMax Foaming Herd Spray was tested at Legacy Farm LLC, Plainview Tex. where an outbreak of hairy heel warts was occurring. Approximately 1000 cattle were treated with a power foamer and HealMax Foaming Herd Spray. Of these 1000 cattle, approximately 9% of the herd exhibited hairy heel wart lesions of various degrees of severity. 30% of cows with hairy heel warts lesions were in advanced stages classified as severe, 45% exhibited lesions that were moderately severe, and 25% of lesions were in the early stages. The foam was applied directly to open wart lesions caused by digital dermatitis while cattle walked to the milking parlor as well as to hooves that were unaffected by lesions. Foam was applied for two consecutive days.

The results showed an overall 81% elimination in hairy heel wart lesions when evaluated by the Hoof Trimmer one week after the second application of the foam with the remaining cows requiring an additional treatment. Of the 19% that required additional treatment, these cows exhibited the most severe heal wart lesions, in some cases with lesions on more than one leg, yet even these cows exhibited post treated lesions that were either partially scabbed or reduced in size. One or two additional product applications would constitute an additional treatment needed to fully scab and therefore complete the enclosure of the open lesion.

Moreover, of the 910 cows that were treated but did not have hairy heel wart lesions, there were no reports of new heal wart lesions of any stage of severity. Of the 27 cows with severe hairy heel wart lesions, 8 cows (30% of severe group) required further treatment to ensure complete closure of the lesion, the remaining cows exhibited closed, scabbed lesions, requiring no further treatment. Of the 40 cows with moderately severe lesions, 6 cows (15% of moderately severe group) required further treatments while the remaining 36 cows showing closed, scabbed, lesions. Of the 23 cows with early stage hairy heel wart lesions, 3 cows (13% of early stage) required further treatment.

These results demonstrate that, similar to application via spray, application of the presently taught composition via foam is an effective means to treat and/or prevent one or more infectious diseases of the hoof in animals, including hairy heel warts. Unlike the first product trial, these cows were treated during regular production versus being sequestered and then treated on a trimming table. The lesions and hooves were initially sprayed with water from a hose but at a proximity that would not ensure all dirt and debris were cleared from the lesion. Furthermore, because the cows were standing, it was difficult to clear all debris and likewise it was more challenging to ensure complete product coverage. Nonetheless, the results demonstrate that the product is highly effective when used during the daily production routine for treatment and/or prevention of an active infectious disease, such as hairy heel warts.

The effectiveness of HealMax Foaming Herd Spray was found to at least approximately parallel HealMax Herd Spray, albeit the foam application method for the customer was better suited for their dairy operation. Large dairy operations benefit from foaming the product because it can be integrated into their milking routine, foaming uses less product, increased accuracy in achieving thorough contact with lesion. Also, dairy farm management can quickly see that cows are being properly treated with Healmax by the milking staff. The foam may be able to better handle dirt and debris because the foam has additional cling and continues to deliver fresh product as the foam breaks down into liquid.

Application of HealMax Foaming Herd Spray allows, inter alia, for more accurate application due to visibility, less product usage, and the ability to treat areas difficult to reach such as underneath the hoof or between cloves of the hoof. Foaming is safe because it reduces the opportunity for a highly concentrated stream of product with sticking capability to hit a worker in the face/eye. Although no direct detailed comparison experiments were done to compare the presently taught spray formulation with the presently taught foam formulation, given that similar to the spray formulation the foam works highly effectively, one would expect the results of HealMax Foam to be the similar if not the same as those observed with HealMax Spray formulations. This would be expected so long as a similar if not identical concentration of active ingredient was used and a similar application protocol was used of first cleaning the treatment region with water and allowing 5-10 minutes of application time after initial contact.

7.4 Example 4

Addition of Anaesthetic

Trials are conducted where a numbing agent is added to the novel composition taught herein. The numbing agent, Lidocaine, at the rate of 2.5% is added to the formulation. HealMax may sting for several minutes when applied to an open sore. While stinging is much less severe than other products such as acidified copper, in some cases, it may agitate the cow thus causing it to kick or move more than normal. This could cause potential harm to the individual spraying or if in the milking parlor the milking equipment could be knocked loose from the udders. Testing of a formulation which includes a numbing agent, Lidocaine, to reduce stinging sensation is carried out. A stable HealMax solution with the addition of lidocaine hydro chloride monohydrate USP at the rate of addition of 2.5% has been produced. This product is tested to determine if stinging sensation is mitigated by the addition of a numbing agent such as lidocaine. This is accomplished by observing the comfort level of a cow directly after spraying. The numbing agent has a beneficial and desirable effect because, inter alia, it numbs the treated site and reduces any pain or irritation caused to the ungulate by application of the presently taught compositions.

The invention claimed is:

1. A method for treating an animal that has or is at risk for one or more infectious diseases of the hoof, wherein said infectious disease comprises an open lesion on the lower leg and/or hoof area of said animal, said method comprising:
administering to a lower leg and/or hoof area of said animal copper-free and zinc-free composition comprising at least one aldehyde, wherein the aldehyde is not formaldehyde,
and wherein the composition comprises an effective amount of said aldehyde such that if an animal has the one or more infectious diseases, the composition causes formation of a scab over the lesion.

2. The method of claim 1, wherein said infectious disease of the foot is hairy heel warts, foot rot, stable foot rot, or foot scald.

3. The method of claim 1, wherein the animal is an ungulate.

4. The method of claim 1, wherein said administering step is in the form of a spray or foam, or a mixture thereof.

5. The method of claim 1, wherein about three to about ten milliliters of said composition is sprayed on to the lower leg and/or hoof area of the animal.

6. The method of claim 1, wherein said infectious disease comprises an open lesion on the lower leg and/or hoof area of said animal, and wherein about five to about fifteen minutes after the administering step, said composition causes the formation of a scab over said lesion.

7. The method of claim 1, wherein said composition comprises about 5% to about 30% by weight of at least one aldehyde; about 5% to 20% by weight of at least one quaternary ammonium compound; about 0.03% to 3% by weight of at least one poly(alkylene glycol) alkyl ether; about 0.03% to 3% by weight of at least one gelling agent; about 0.03% to 3% by weight of at least one antimicrobial essential oil or active thereof; and about 0.03% to 5% by weight of at least one surfactant.

8. The method of claim 1, wherein the composition further comprises at least one antimicrobial essential oil or at least one active thereof or a mixture thereof.

9. The method of claim 1, wherein the composition further comprises at least one poly(alkylene glycol) alkyl ether.

10. The method of claim 1, wherein the composition further comprises at least one gelling agent.

11. The method of claim 1, wherein the composition further comprises at least one quaternary ammonium compound.

12. The method of claim 1, wherein the composition further comprises at least one surfactant.

13. The method of claim 1, wherein the composition further comprises one or more ethoxylated nonlyphenols.

14. The method of claim 1, wherein the composition, further comprises: one or more quaternary ammonium compounds; one or more gelling agents; one or more surfactants; one or more antimicrobial essential oils or actives thereof; and one or more poly(alkylene glycol) alkyl ethers.

15. The method of claim 1, wherein said aldehyde is selected from the group consisting of: glyceraldehyde, glutaraldehyde, dextran dialdehyde, and carbohydrates.

16. The method of claim 1, wherein said at least one aldehyde comprises glutaraldehyde.

17. The method of claim 1, wherein said at least one aldehyde comprises glutaraldehyde and glyoxal.

18. The method of claim 1, wherein the composition further comprises glyoxal.

19. The method of claim 1, wherein said administering step is in the form of a foot bath, wherein said animal walks through the foot bath.

20. The method of claim 1, wherein said at least one aldehyde comprises glutaraldehyde and phthaldehyde.

* * * * *